(12) United States Patent
Khodakovskaya et al.

(10) Patent No.: US 11,326,145 B2
(45) Date of Patent: May 10, 2022

(54) METHOD FOR APPLICATIONS OF NANO-SIZED MATERIALS AS CELL GROWTH REGULATORS / CELL GROWTH ENHANCERS FOR PLANT, AND AGENT INCLUDING NANO-SIZED MATERIALS

(71) Applicant: BOARD OF TRUSTEES OF THE UNIVERSITY OF ARKANSAS, Little Rock, AR (US)

(72) Inventors: Mariya Khodakovskaya, Little Rock, AR (US); Diamond McGehee, Conway, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 149 days.

(21) Appl. No.: 16/013,311

(22) Filed: Jun. 20, 2018

(65) Prior Publication Data

US 2018/0312804 A1 Nov. 1, 2018

Related U.S. Application Data

(63) Continuation-in-part of application No. 14/185,423, filed on Feb. 20, 2014, now abandoned.

(60) Provisional application No. 61/766,799, filed on Feb. 20, 2013.

(51) Int. Cl.
*C12N 5/04* (2006.01)
*A01H 3/00* (2006.01)
*A01H 4/00* (2006.01)

(52) U.S. Cl.
CPC ............. *C12N 5/04* (2013.01); *A01H 3/00* (2013.01); *A01H 4/001* (2013.01)

(58) Field of Classification Search
CPC .......................................................... C12N 5/04
See application file for complete search history.

(56) References Cited

PUBLICATIONS

Khodakovskaya et al (Carbon Nanotubes Induce Growth Enhancement of Tobacco Cells. American Chemistry Society 6: 2128-2135, published online Feb. 23, 2012) (Year: 2012).*
Mondal et al (Beneficial role of carbon nanotubes on mustard plant growth: an agricultural prospect. J Nanopart Res, 13:4519-4528, 2011) (Year: 2011).*
Wang et al (Multi-walled carbon nanotubes can enhance root elongation of wheat (Triticum aestivum) plants. J Nanopart Res. 14: 841, 2012) (Year: 2012).*
Morris et al (Regulation of product synthesis in cell cultures of Catharanthus roseus. Effect of culture temperature. Plant Cell Reports. 5:427-429, 1986). (Year: 1986).*
Misawa (Plant Tissue Culture: An Alternative for Production of Useful Metabolite), chapter 6, 1994) teaching/suggest using activated carbon/charcoal in Catharanthus cells. (Year: 1994).*
Liu et al (Synthesis and characterization of graphene and carbon nanotubes: A review on the past and recent developments. Journal of Industrial and Engineering Chemistry. 1175-1185, 2014 (Year: 2014).*
Wang et al (Phytotoxicity of Graphene Family Nanomaterials and Its Mechanisms: A Review. Front. Chem., 01, 2019) (Year: 2019).*
Tan et al (Studies on toxicity of multi-wall carbon nanotubes on suspension rice Cells. Dec. 2009) (Year: 2009).*
Lin et al (Studies on toxicity of multi-walled carbon nanotubes on *Arabidopsis* T87 suspension cells. Journal of Hazardous Materials . 170: 578-583, 2009) (Year: 2009).*
Serag et al (Nanobiotechnology meets plant cell biology: carbon nanotubes as organelle targeting nanocarriers. RSC Adv., 4856-4862, published Dec. 2012) (Year: 2012).*
Shams et al (Isolation and Characterization of Antineoplastic Alkaloids from *Catharanthus roseus* L. Don. Cultivated in Egypt. Afr J Tradit Complement Altern Med. 6: 118-122, 2009) (Year: 2009).*
Khodakovskaya et al (Complex genetic, photothermal, and photoacoustic analysis of nanoparticle-plant interactions. PNAS. 108: 1028-1033, 2011) (Year: 2011).*
Shilpa et al (An Alternate Method of Natural Drug Production: Elciting Secondary Metabolite Production Using Plant Cell Culture. Journal of Plant Sciences 5 (3): 222-247, 2010) (Year: 2010).*
Smetanska (Production of Secondary Metabolites Using Plant Cell Cultures. Adv Biochem Engin/Biotechnol 111: 187-228, 2008) (Year: 2008).*
Kumar, S.; Bajpai, V.; Singh, A.; Kumar, B. Identification, Characterization and Distribution of Terpene Indole Alkaloids in Ethanolic Extracts of Catharanthus Roseus Using HPLC/ESI-QTOF-MS/MS and the Study of Their Geographical Variation. Rapid Commun. Mass Spectrom. 2017 DOI: 10.1002/rcm.8037.

(Continued)

*Primary Examiner* — Bratislav Stankovic
*Assistant Examiner* — Wayne Zhong
(74) *Attorney, Agent, or Firm* — Locke Lord LLP; Tim Tingkang Xia, Esq.

(57) ABSTRACT

One aspect of the disclosure is directed to a method for activation/enhancement of cell growth of a plant. The method also stimulates the production of pharmaceutically active metabolites, including alkaloids, in plant cell cultures. The method includes providing a nano-sized material contained agent, and treating the plant with the nano-sized material contained agent to allow sufficient interaction of cells of the plant with the nano-sized material so as to activate/enhance the cell growth of the plant or to stimulate the production of pharmaceutically active metabolites.

10 Claims, 13 Drawing Sheets

Specification includes a Sequence Listing.

(56) References Cited

PUBLICATIONS

Monforte González, M.; Ayora Talavera, T.; Maldonado Mendoza, I. E.; Loyola Vargas, V. M. Quantitative Analysis of Serpentine and Ajmalicine in Plant Tissues of Catharanthus Roseus and Hyoscyamine and Scopolamine in Root Tissues of Datura Stramonium by Thin Layer Chromatography densitometry Phytochem. Anal. 1992, 3 (3), 117-121 DOI: 10.1002/pca.2800030305.

* cited by examiner

SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: Forward primer for NtLRX1

<400> SEQUENCE: 1
agccaccacc atacacacct caat                                          24

<210> SEQ ID NO 2
<211> LENGTH: 24
<212> TYPE: DNA
<213> ORGANISM: Artificial Sequence
<220> FEATURE:
<223> OTHER INFORMATION: Reverse primer for NtLRX1

<400> SEQUENCE: 2
tggtggtgaa gacggtgtca cata                                          24

<210> SEQ ID NO 3
<211> LENGTH: 24
<212> TYPE: DNA
<213> ORGANISM: Artificial Sequence
<220> FEATURE:
<223> OTHER INFORMATION: Forward primer for NtPIP1

<400> SEQUENCE: 3
ggttcatttg gccaccatcc caat                                          24

<210> SEQ ID NO 4
<211> LENGTH: 24
<212> TYPE: DNA
<213> ORGANISM: Artificial Sequence
<220> FEATURE:
<223> OTHER INFORMATION: Reverse primer for NtPIP1

<400> SEQUENCE: 4
gcagcaagag cagctccaat gaat                                          24

<210> SEQ ID NO 5
<211> LENGTH: 24
<212> TYPE: DNA
<213> ORGANISM: Artificial Sequence
<220> FEATURE:
<223> OTHER INFORMATION: Forward primer for CycB

<400> SEQUENCE: 5
ttctggctga gctgggattg atga                                          24

<210> SEQ ID NO 6
<211> LENGTH: 24
<212> TYPE: DNA
<213> ORGANISM: Artificial Sequence

```
<220> FEATURE:
<223> OTHER INFORMATION: Reverse primer for CycB

<400> SEQUENCE: 6
tgatggtgtg tcgagcagca taga                                              24

<210> SEQ ID NO 7
<211> LENGTH: 24
<212> TYPE: DNA
<213> ORGANISM: Artificial Sequence
<220> FEATURE:
<223> OTHER INFORMATION: Forward primer for Actin

<400> SEQUENCE: 7
gaacgggaaa ttgtccgcga tgtt                                              24

<210> SEQ ID NO 8
<211> LENGTH: 24
<212> TYPE: DNA
<213> ORGANISM: Artificial Sequence
<220> FEATURE:
<223> OTHER INFORMATION: Reverse primer for Actin

<400> SEQUENCE: 8
atggtaatga cctgcccatc tggt                                              24

<210> SEQ ID NO 9
<211> LENGTH: 11
<212> TYPE: PRT
<213> ORGANISM: Nicotiana tabacum

<400> SEQUENCE: 9

Asp Ala Lys Arg Asn Ala Arg Asp Ser His Val
1               5                   10
```

METHOD FOR APPLICATIONS OF NANO-SIZED MATERIALS AS CELL GROWTH REGULATORS / CELL GROWTH ENHANCERS FOR PLANT, AND AGENT INCLUDING NANO-SIZED MATERIALS

CROSS-REFERENCE TO RELATED PATENT APPLICATIONS

This application is a continuation-in-part of U.S. patent application Ser. No. 14/185,423, filed Feb. 20, 2014, which claims priority to and the benefit of U.S. provisional patent application Ser. No. 61/766,799, filed Feb. 20, 2013, entitled "APPLICATIONS OF CARBON NANOTUBES AS GROWTH REGULATORS/GROWTH ENHANCERS," by Mariya V. Khodakovskaya and Alexandru S. Biris, which is incorporated herein in its entirety by reference.

Some references, which may include patents, patent applications and various publications, are cited and discussed in the description of this invention. The citation and/or discussion of such references is provided merely to clarify the description of the disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [13] represents the 13th reference cited in the reference list, namely, Khodakovskaya, M.; de Silva, K.; Nedosekin, D.; Dervishi, E.; Biris, A. S.; Shashkov, E. V.; Galanzha, E. I.; Zharov, V. P. Complex genetic, photothermal, and photoacoustic analysis of nanoparticle-plant interactions. PNAS 2011, 108, 1028-1033.

FIELD OF THE DISCLOSURE

The disclosure relates generally to applications of nano-sized materials, and more particularly to a method for applications of nano-sized materials as cell growth regulators/cell growth enhancers for a plant, and an agent including the nano-sized materials. The method can also stimulate the production of pharmaceutically active metabolites, including alkaloids, in plant cell cultures.

BACKGROUND OF THE DISCLOSURE

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the disclosure.

Large scale plant tissue culture is an attractive alternative to the traditional methods of plantation, as it offers advantages of controlled supply of biochemicals independent of plant availability and well defined production systems which result in higher yields and more consistent quality of the product. During the last 30 years, plant cell and tissue cultures have been comprehensively studied for the production of secondary metabolites. However, despite promising results, this technology has led to only a few realizations for the production of commercial compounds, at the industrial scale. This lack of industrial success can be attributed to severe bottlenecks that have been identified during the last decades. Among them are insufficient knowledge on the biosynthetic pathways leading to erratic production and poor biomass productivity.

Novel discoveries in the area of nanotechnology have provided advanced knowledge and technological platforms with applications in a variety of scientific areas, ranging from medicine, aerospace, electronics and sensing to defense industries [1-3]. Lately, given the need to understand the interaction between engineered nano-sized materials and various biological systems, a significant research interest has developed around the use of nanotechnology-based approaches for agricultural and food systems [4]. The unique properties of nano-sized materials make them an attractive tool for crop management techniques. In this respect, it has been documented that nanoparticles can be beneficial for the delivery of biological molecules into plant cells [5-8] or to improve herbicide delivery [9]. Specific types of nanoparticles in low doses have not been found harmful to plants but instead are capable of activating specific physiological processes. For instance, $TiO_2$ nanoparticles (0.25-4%) are able to promote photosynthesis and nitrogen metabolism in spinach and therefore improve growth of the plants [10, 11]. The inventors have demonstrated recently that multi-walled carbon nanotubes (MWCNTs) at relatively low doses (10-40 µg/mL) can penetrate thick seed coats, stimulate germination, and activate enhanced growth in tomato plants [12, 13]. All of these developments have the potential to transform agricultural practices in the near future and to provide solutions to some of the most serious problems related to plant growth and development. Thus, there is a constant search for compounds that can significantly activate cell division in cultures of valuable plant cells. However, discovered compounds such as phytohormones, precursors of metabolic pathways are not always effective in the industrial scale.

Therefore, a heretofore unaddressed need exists in the art to address the aforementioned deficiencies and inadequacies.

SUMMARY OF THE DISCLOSURE

Certain aspects of the disclosure are directed to applications of carbon-based nanomaterials to stimulate production of pharmaceutically active metabolites (secondary metabolites) in plant cell cultures.

In one aspect, the disclosure relates to a method for stimulating production of pharmaceutically active metabolites (secondary metabolites) in plant cell cultures. In one embodiment, the method includes providing a cell culture having one or more cells of the plant, introducing an amount of a nano-sized material into the cell culture to form a mixture thereof, maintaining the mixture at a temperature for a period of time to allow sufficient interaction of the one or more cells with the nano-sized material so as to enhance the production of a pharmaceutically active metabolite in the cell culture, and extracting the pharmaceutically active metabolite from plant cell cultures.

In one embodiment, the method for stimulating production of pharmaceutically active metabolites (secondary metabolites) in plant cell cultures further includes the step of providing the cell culture: germinating seeds of the plant in a Murashige-Skoog (MS) medium to establish calli of the plant; and maintaining the callus culture at a predetermined condition to produce the cell culture having the one or more cells of the plant.

In some embodiments, the amount of the nano-sized material in the method for stimulating production of pharmaceutically active metabolites (secondary metabolites) in plant cell cultures has a concentration in a range of about 5 to about 500 μg/mL in the cell culture, a concentration in a range of about 25 to about 500 μg/mL in the cell culture, a concentration in a range of about 25 to about 200 μg/mL in the cell culture, a concentration in a range of about 25 to about 150 μg/mL in the cell culture, a concentration in a range of about 50 to about 150 μg/mL in the cell culture, or a concentration in a range of about 50 to about 100 μg/mL in the cell culture.

In some embodiments, the nano-sized material in the method for stimulating production of pharmaceutically active metabolites (secondary metabolites) in plant cell cultures is carbon-based nanomaterials including, but not limited to, single or multi-walled nanotubes, graphene, fullerenes, carbon nanofibers, and nanodiamonds.

In one embodiment, the plant in the method for stimulating production of pharmaceutically active metabolites is *Catharanthus* including, but not limited to, *Catharanthus roseus*.

In one embodiment, the method stimulates the production of alkaloids in plant cell cultures. The alkaloids include, but not limited to, vinblastine, vincristine, morphine, quinine, strychnine, and ephedrine.

In one embodiment, the method for stimulating production of pharmaceutically active metabolites (secondary metabolites) in plant cell is cultured in the light cultivation condition. In another embodiment, the method for stimulating production of pharmaceutically active metabolites (secondary metabolites) in plant cell is cultured in the dark cultivation condition.

Certain aspects of the disclosure are directed to applications of carbon nanotubes as regulators of seed germination and plant growth.

In one aspect, the disclosure relates to a method for activation/enhancement of cell growth of a plant. In one embodiment, the method includes providing a cell culture having one or more cells of the plant, introducing an amount of a nano-sized material into the cell culture to form a mixture thereof, and maintaining the mixture at a temperature for a period of time to allow sufficient interaction of the one or more cells with the nano-sized material so as to activate/enhance the cell growth of the plant.

In one embodiment, the interaction of the one or more cells with the nano-sized material increases expression levels of one or more marker genes of the plant, where the one or more marker genes are essential for the cell growth of the plant. The one or more marker genes of the plant includes at least one of a CycB gene, and an NtLRX1 (extensin1) gene, and an NtPIP1 (aquaporin) gene.

In one embodiment, the nano-sized material includes nanotubes. In one embodiment, the nano-sized material includes single-wall carbon nanotubes, or multi-walled carbon nanotubes, or a combination of them.

In one embodiment, the amount of the nano-sized material is introduced such that the mixture has a concentration of the nano-sized material in a range of 0.1-1000 μg/mL.

In one embodiment, the temperature is in a range of 5-35° C., and the period of time is in a range from 0.1 hours to 2 months.

In one embodiment, the step of providing the cell culture includes germinating seeds of the plant in a Murashige-Skoog (MS) medium with about 0.8% agar to establish calli of the plant, transferring the established calli to a fresh MS medium with about 0.8% agar, about 2% sucrose, and about 1 mg/l 2,4-dichlorophenoxyacetic acid (2,4-D) to produce a callus culture of the plant, and maintaining the callus culture at a predetermined condition to produce the cell culture having the one or more cells of the plant.

In another aspect, the disclosure relates to a method for activation/enhancement of cell growth of a plant. In one embodiment, the method includes providing a growth medium, introducing an amount of a nano-sized material into the growth medium to form a nano-sized material contained agent, and treating the plant with the nano-sized material contained agent to allow sufficient interaction of cells of the plant with the nano-sized material so as to activate/enhance the cell growth of the plant.

In one embodiment, the step of treating the plant with the nano-sized material contained agent includes germinating seeds of the plant in the nano-sized material contained agent.

In another embodiment, the step of treating the plant with the nano-sized material contained agent includes soaking seeds of the plant in the nano-sized material contained agent before planting the seeds in soil.

In yet another embodiment, the step of treating the plant with the nano-sized material contained agent includes applying a desired amount of the nano-sized material contained agent to leaves, stems and/or roots of the plant.

In one embodiment, the interaction of the cells with the nano-sized material increases expression levels of one or more marker genes of the plant, where the one or more marker genes are essential for the cell growth of the plant. The one or more marker genes of the plant includes at least one of a CycB gene, and an NtLRX1 (extensin1) gene, and an NtPIP1 (aquaporin) gene.

In one embodiment, the nano-sized material includes nanotubes. In one embodiment, the nano-sized material includes single-wall carbon nanotubes, or multi-walled carbon nanotubes, or a combination of them.

In one embodiment, the nano-sized material contained agent has a concentration of the nano-sized material in a range of 0.1-1000 μg/mL.

In one embodiment, the growth medium includes an MS medium with about 0.8% agar, about 2% sucrose, and about 1 mg/l 2,4-D.

In yet another aspect, the disclosure relates to a method for activation/enhancement of cell growth of a plant. In one embodiment, the method includes providing a nano-sized material contained agent, and treating the plant with the nano-sized material contained agent to allow sufficient interaction of cells of the plant with the nano-sized material so as to activate/enhance the cell growth of the plant.

In one embodiment, the step of treating the plant with the nano-sized material contained agent includes germinating seeds of the plant in the nano-sized material contained agent.

In another embodiment, the step of treating the plant with the nano-sized material contained agent includes soaking seeds of the plant in the nano-sized material contained agent before planting the seeds in soil.

In a further embodiment, the step of treating the plant with the nano-sized material contained agent includes applying a desired amount of the nano-sized material contained agent to leaves, stems and/or roots of the plant.

In one embodiment, the interaction of the cells with the nano-sized material increases expression levels of one or more marker genes of the plant, wherein the one or more marker genes are essential for the cell growth of the plant. In one embodiment, the one or more marker genes of the plant includes at least one of a CycB gene, and an NtLRX1 (extensin1) gene, and an NtPIP1 (aquaporin) gene.

In one embodiment, the step of providing the nano-sized material contained agent includes providing a growth medium, and introducing an amount of a nano-sized material into the growth medium to form the nano-sized material contained agent, where the nano-sized material contained agent has a concentration of the nano-sized material in a range of 0.1-1000 µg/mL.

In one embodiment, the nano-sized material includes nanotubes. In one embodiment, the nano-sized material includes single-wall carbon nanotubes, or multi-walled carbon nanotubes, or a combination of them.

In one embodiment, the growth medium includes an MS medium with about 0.8% agar, about 2% sucrose, and about 1 mg/l 2,4-D.

In a further aspect, the disclosure relates to an agent for activation/enhancement of cell growth of a plant. In one embodiment, the agent includes a growth medium, and a nano-sized material added into the growth medium. The agent has a concentration of the nano-sized material in a range of 0.1-1000 µg/mL.

In use, the agent is applied to the plant with the nano-sized material contained agent to allow sufficient interaction of cells of the plant with the nano-sized material so as to activate/enhance the cell growth of the plant. In one embodiment, seeds of the plant are germinated in the nano-sized material contained agent. In another embodiment, seeds of the plant are soaked in the nano-sized material contained agent before the seeds are planted in soil. In a further embodiment, leaves, stems and/or roots of the plant are treated with a desired amount of the nano-sized material contained agent.

In one embodiment, the interaction of the cells with the nano-sized material increases expression levels of one or more marker genes of the plant, wherein the one or more marker genes are essential for the cell growth of the plant. The one or more marker genes of the plant includes at least one of a CycB gene, and an NtLRX1 (extensin1) gene, and an NtPIP1 (aquaporin) gene.

In one embodiment, the nano-sized material includes nanotubes. The nano-sized material includes single-wall carbon nanotubes, or multi-walled carbon nanotubes, or a combination of them.

In one embodiment, the growth medium includes an MS medium with about 0.8% agar, about 2% sucrose, and about 1 mg/l 2,4-D.

According to embodiments of the disclosure, multi-walled carbon nanotubes (MWCNTs) have the ability to enhance the growth of tobacco cell culture (about 55-64% increase over control) in a wide range of concentrations (about 5-500 µg/mL). Activated carbon (AC) stimulated cell growth (about 16% increase) only at low concentrations (about 5 µg/mL) while dramatically inhibited the cellular growth at higher concentrations (about 100-500 µg/mL). A correlation between the activation of cells growth exposed to MWCNTs and the up-regulation of genes involved in cell division/cell wall formation and water transport are obtained. The expression of the tobacco aquaporin (NtPIP1) gene, as well as production of the NtPIP1 protein, significantly increased in cells exposed to MWCNTs compared to control cells or those exposed to AC. The expression of marker genes for cell division (CycB) and cell wall extension (NtLRX1) was also up-regulated in cells exposed to MWCNTs compared to control cells or those exposed to activated carbon only.

These and other aspects of the disclosure will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Figure 1:
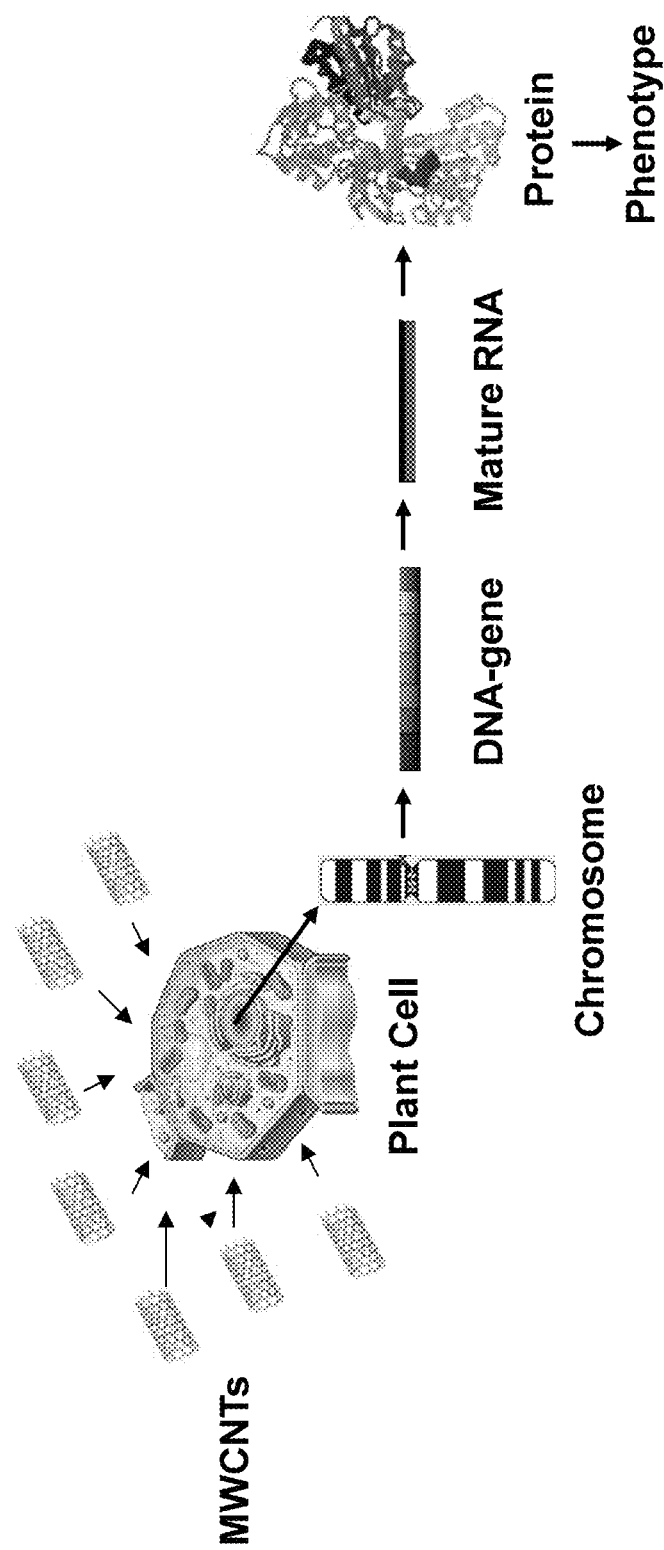
FIG. 1 shows a schematic representation of the complex effects that multi-walled carbon nanotubes (MWCNTs) can induce at the cellular and molecular levels in living organisms according to certain embodiments of the disclosure. Interaction of plant cells with MWCNTs can lead to significant changes at the molecular level and affect the expression of specific genes and the production of proteins responsible for a particular phenotype.

The disclosure will now be described more fully hereinafter with reference to the accompanying drawings, in which exemplary embodiments of the disclosure are shown. This invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the disclosure or of any exemplified term. Likewise, the disclosure is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the disclosure.

As used herein, the term, "nano-sized material", refers to an object of intermediate size between molecular and microscopic (micrometer-sized) materials. In describing nano-sized materials, the sizes of the nano-sized materials refer to the number of dimensions on the nanoscale. For example, nanotextured surfaces have one dimension on the nanoscale, i.e., only the thickness of the surface of an object is between 1.0 and 1000.0 nm. Nanowires have two dimensions on the nanoscale, i.e., the diameter of the tube is between 1.0 and 1000.0 nm; its length could be much greater. Finally, sphere-like nanoparticles have three dimensions on the nanoscale, i.e., the particle is between 1.0 and 1000.0 nm in each spatial dimension. A list of nano-sized materials includes, but are not limited to, nanoparticle, nanocomposite, quantum dot, nanofilm, nanoshell, nanofiber, nanowire, nanotree, nanobush, nanotube, nanoring, nanorod, and so on.

As used herein, the term, "secondary metabolites in plants", refers to a large number of specialized compounds that do not aid in the growth and development of plants but are required for the plant to survive in its environment. Plant secondary metabolites can be divided into three major groups: flavonoids and allied phenolic and polyphenolic compounds, terpenoids and nitrogen-containing alkaloids and sulphur-containing compounds.

As used herein, the term, "alkaloid", refers to any of a class of naturally occurring organic nitrogen-containing bases. Alkaloids have diverse and important physiological effects on humans and other animals. Some pharmaceutical active alkaloids are vinblastine, vincristine, morphine, quinine, strychnine, and ephedrine. Alkaloids are found primarily in plants and are especially common in certain families of flowering plants.

The description below is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the disclosure.

Overview

Nano-sized materials have the unique properties including, but are not limited to, small size, high bio-chemical reactivity, ability to penetrate cells, and swift distribution inside organisms, which make them an attractive tool for crop management techniques. Perspectives on nano-biotechnological approaches for the regulation of plant productivity depend on a thorough understanding of the molecular mechanism of activation of seed germination and plant growth in the presence of complex engineered nano-sized materials. The inventors demonstrated earlier that multiwalled carbon nanotubes (MWCNTs) at relatively low doses (10-40 μg/ml) can penetrate thick seed coats, stimulate germination, activate enhanced growth of tomato plants [12, 13], and affect their total gene expression [13]. For example, the expression of tomato aquaporin (water channel gene) and a number of other genes related to plant responses to environmental stress were found to be up-regulated in tomato seedlings by exposure to MWCNTs, but not by exposure to activated carbon (AC), alone. To further understand the biological mechanisms that control the complex influence of carbon nanotubes on plants, the interactions between these tubular nanostructures and plants need to be investigated at all levels of plant organization, including the cell, transcriptome, and proteome.

To achieve this goal, the following strategy is applied according to embodiments of the disclosure. First, on the basis of phenotypic traits of the biological organism exposed to nano-sized materials, the involvement of nano-sized materials in specific cellular, developmental, signaling, or biosynthetic processes and pathways can be hypothesized. Next, key genes involved in such processes need to be identified as markers of selected biological processes. The expression of marker genes has to be studied in organisms exposed and unexposed to nano-sized materials. As the next step, the expression level of the products of the marker genes (proteins) has to be monitored in tested organisms. According to the disclosure, the strategy is applicable to any biological system that is exposed to nano-sized materials for characterizing the molecular mechanisms of positive or negative (toxic) effects of the nano-sized materials observed in the nano-sized material exposed biological system.

As shown in FIG. 1, the MWCNTs can affect the plant in different levels, for example, from plant level (phenotype of the plant), from cell level, from gene level, and from protein level. A plant has many plant cells. A plant cell has a genome. The genome includes chromosomes. A chromosome may have many genes. A gene can be used to create a mature RNA through transcription. A mature RNA can be used to express a protein through translation. The expressed proteins can affect the phenotype of the plant. When the MWCNTs affect the expression of certain proteins, the phenotype of the plant can be changed. For example, if the expression of NtPIP1 protein or/and the NtLRX1 protein is increased by adding MWCNTs, the plant or the cell growth are stimulated.

Certain aspects of the disclosure are directed to applications of carbon-based nanomaterials to stimulate production of pharmaceutically active metabolites (secondary metabolites) in plant cell cultures.

In one aspect, the disclosure relates to a method for stimulating production of pharmaceutically active metabolites (secondary metabolites) in plant cell cultures. In one embodiment, the method includes providing a cell culture having one or more cells of the plant, introducing an amount of a nano-sized material into the cell culture to form a mixture thereof, maintaining the mixture at a temperature for a period of time to allow sufficient interaction of the one or more cells with the nano-sized material so as to enhance the production of a pharmaceutically active metabolite in the cell culture, and extracting the pharmaceutically active metabolite from plant cell cultures.

In one embodiment, the method for stimulating production of pharmaceutically active metabolites (secondary metabolites) in plant cell cultures further includes the step of providing the cell culture: germinating seeds of the plant in a Murashige-Skoog (MS) medium to establish calli of the plant; and maintaining the callus culture at a predetermined condition to produce the cell culture having the one or more cells of the plant.

In some embodiments, the amount of the nano-sized material in the method for stimulating production of pharmaceutically active metabolites (secondary metabolites) in plant cell cultures has a concentration in a range of about 5 to about 500 μg/mL in the cell culture, a concentration in a range of about 25 to about 500 μg/mL in the cell culture, a concentration in a range of about 25 to about 200 μg/mL in the cell culture, a concentration in a range of about 25 to about 150 μg/mL in the cell culture, a concentration in a range of about 50 to about 150 μg/mL in the cell culture, or a concentration in a range of about 50 to about 100 μg/mL in the cell culture.

In some embodiments, the nano-sized material in the method for stimulating production of pharmaceutically active metabolites (secondary metabolites) in plant cell cultures is carbon-based nanomaterials including, but not limited to, single or multi-walled nanotubes, graphene, fullerenes, carbon nanofibers, and nanodiamonds.

In one embodiment, the plant in the method for stimulating production of pharmaceutically active metabolites is *Catharanthus* including, but not limited to, *Catharanthus roseus*.

In one embodiment, the method stimulates the production of alkaloids in plant cell cultures. The alkaloids include, but not limited to, vinblastine, vincristine, morphine, quinine, strychnine, and ephedrine.

In one embodiment, the method for stimulating production of pharmaceutically active metabolites (secondary metabolites) in plant cell is cultured in the light cultivation condition. In another embodiment, the method for stimulating production of pharmaceutically active metabolites (secondary metabolites) in plant cell is cultured in the dark cultivation condition.

Certain aspects of the disclosure are directed to applications of carbon nanotubes as regulators of seed germination and plant growth.

In one aspect of the disclosure, the method for activation/enhancement of cell growth of a plant includes providing a cell culture having one or more cells of the plant, introducing an amount of a nano-sized material into the cell culture to form a mixture thereof, and maintaining the mixture at a temperature for a period of time to allow sufficient interaction of the one or more cells with the nano-sized material so as to activate/enhance the cell growth of the plant. In certain embodiments, the temperature is in a range of 5-35° C., and the period of time is in a range from 0.1 hours to 2 months. In certain embodiments, the mixture has a concentration of the nano-sized material in a range of 0.1-1000 μg/mL.

According to the disclosure, the interaction of the one or more cells with the nano-sized material increases expression levels of one or more marker genes of the plant, where the one or more marker genes are essential for the cell-wall assembly, cell division and/or cell growth of the plant. The one or more marker genes of the plant includes, but are not limited to, a CycB gene, and an NtLRX1 (extensin1) gene, and/or an NtPIP1 (aquaporin) gene. It should be noted that other marker genes of the plant can also be utilized to practice this invention.

The nano-sized material includes nanotubes, such as single-wall carbon nanotubes (SWCNTs), or MWCNTs, or a combination of them. In the exemplary examples disclosed in the disclosure, MWCNTs are utilized to practice the invention. It should be appreciated that other types of nano-sized materials can also be utilized to practice the invention.

In certain embodiments, the step of providing the cell culture includes germinating seeds of the plant in a Murashige-Skoog (MS) medium with about 0.8% agar to establish calli of the plant, transferring the established calli to a fresh MS medium with about 0.8% agar, about 2% sucrose, and about 1 mg/l 2,4-dichlorophenoxyacetic acid (2,4-D) to produce a callus culture of the plant, and maintaining the callus culture at a predetermined condition to produce the cell culture having the one or more cells of the plant.

Another aspect of the disclosure is directed to a method for activation/enhancement of cell growth of a plant, which includes providing a growth medium, introducing an amount of a nano-sized material into the growth medium to form a nano-sized material contained agent, and treating the plant with the nano-sized material contained agent to allow sufficient interaction of cells of the plant with the nano-sized material so as to activate/enhance the cell growth of the plant. In certain embodiments, the growth medium comprises an MS medium with about 0.8% agar, about 2% sucrose, and about 1 mg/l 2,4-D. In certain embodiments, the nano-sized material contained agent has a concentration of the nano-sized material in a range of 0.1-1000 µg/mL.

In certain embodiments, the step of treating the plant with the nano-sized material contained agent includes germinating seeds of the plant in the nano-sized material contained agent.

In certain embodiments, the step of treating the plant with the nano-sized material contained agent includes soaking seeds of the plant in the nano-sized material contained agent before planting the seeds in soil.

In certain embodiments, the step of treating the plant with the nano-sized material contained agent includes applying a desired amount of the nano-sized material contained agent to leaves, stems and/or roots of the plant.

A further aspect of the disclosure is also directed to a method for activation/enhancement of cell growth of a plant. In certain embodiments, the method includes providing a nano-sized material contained agent, and treating the plant with the nano-sized material contained agent to allow sufficient interaction of cells of the plant with the nano-sized material so as to activate/enhance the cell growth of the plant.

In certain embodiments, the step of providing the nano-sized material contained agent includes providing a growth medium, and introducing an amount of a nano-sized material into the growth medium to form the nano-sized material contained agent, where the nano-sized material contained agent has a concentration of the nano-sized material in a range of 0.1-1000 µg/mL.

In a further aspect, the disclosure relates to an agent for activation/enhancement of cell growth of a plant. The agent includes a growth medium, and a nano-sized material added into the growth medium. The agent has a concentration of the nano-sized material in a range of 0.1-1000 µg/mL.

In use, the agent is applied to the plant with the nano-sized material contained agent to allow sufficient interaction of cells of the plant with the nano-sized material so as to activate/enhance the cell growth of the plant. In one embodiment, seeds of the plant are germinated in the nano-sized material contained agent. In another embodiment, seeds of the plant are soaked in the nano-sized material contained agent before the seeds are planted in soil. In a further embodiment, leaves, stems and/or roots of the plant are treated with a desired amount of the nano-sized material contained agent.

In certain embodiments, the interaction of the cells with the nano-sized material increases expression levels of one or more marker genes of the plant, wherein the one or more marker genes are essential for the cell growth of the plant. The one or more marker genes of the plant includes at least one of a CycB gene, and an NtLRX1 (extensin1) gene, and an NtPIP1 (aquaporin) gene.

According to embodiments of the disclosure, MWCNTs have the ability to enhance the growth of tobacco cell culture (about 55-64% increase over control) in a wide range of concentrations (about 5-500 µg/mL). Activated carbon (AC) stimulated cell growth (about 16% increase) only at low concentrations (about 5 µg/mL) while dramatically inhibited the cellular growth at higher concentrations (about 100-500 µg/mL). A correlation between the activation of cells growth exposed to MWCNTs and the up-regulation of genes involved in cell division/cell wall formation and water transport are obtained. The expression of the tobacco aquaporin (NtPIP1) gene, as well as production of the NtPIP1 protein, significantly increased in cells exposed to MWCNTs compared to control cells or those exposed to AC. The expression of marker genes for cell division (CycB) and cell wall extension (NtLRX1) was also up-regulated in cells exposed to MWCNTs compared to control cells or those exposed to activated carbon only.

Accordingly, the invention, among other things, has applications in a variety of fields, for example:
  Increase in biomass production of rare/medicinal plants.
  Application to crops growing in drought stress areas (Increase in root length, activation of aquaporins).
  Bioenergy industry in production of algae (source of bioenergy).
  Enhanced production of plant cell cultures (suspensions, callus cultures) for the pharmaceutical industry, agro-biotechnology, or the bioenergy industry.
  Other potential applications include in plant biotechnology, crop management, plant production for non-food use, and the biofuel industry.

Without intent to limit the scope of the disclosure, exemplary examples and their related results according to the embodiments of the disclosure are given below. Note that titles or subtitles may be used in the examples for convenience of a reader, which in no way should limit the scope of the disclosure. Moreover, certain theories are proposed and disclosed herein; however, in no way they, whether they are right or wrong, should limit the scope of the disclosure so long as the disclosure is practiced according to the disclosure without regard for any particular theory or scheme of action.

EXAMPLE

Carbon Nanotubes Induce Growth Enhancement of Tobacco Cells

This study in this exemplary example is the first report, to the inventors' best knowledge, that highlights the positive effects that carbon nano-sized materials have on plant cell division. In this example, the inventors demonstrate for the very first time that the growth of tobacco cell culture (callus) can be affected and highly enhanced by the introduction of multi-walled carbon nanotubes in the growth medium. This effect was in direct correlation with the overexpression of genes-markers for cell division/extension in tobacco cells exposed to MWCNTs. Additionally, analysis of aquaporin gene and protein expression in control and MWCNT-exposed tobacco cells supported a previously formulated hypothesis [13] about the possible regulation of plant water channels (aquaporins) by the exposure to carbon nanotubes. The findings, among other things, represent a significant leap in the understanding of the impact that nano-sized materials have on plants, down to the individual cell level, and contribute to clarification of the molecular mechanisms responsible for the nanotubes' positive impact on plant growth and development.

Materials and Methods

Induction and Cultivation of Tobacco Callus Culture: Seeds of tobacco (cv. Hawana) were sterilized and germinated on Murashige and Skoog (MS) medium with about 0.8% agar. Leaves of 3-week-old sterile tobacco seedlings were cut and placed on the MS medium supplemented with about 2% sucrose and about 1 mg/l of 2,4-dichlorophenoxyacetic acid (2,4-D). For callus induction, leaf explants were cultivated in dark conditions for about 1 month. The established calli were excised from leaves and transferred to fresh MS medium (about 0.8% agar, about 2% sucrose, and about 1 mg/l 2,4-D). The callus cultures were maintained at about 20-22° C. in the dark inside a tissue culture growth chamber.

Induction and Cultivation of *Catharanthus Roseus* Callus Culture: The seeds were surface-sterilized, first in 70% (v/v) ethanol for 30 s, then in a 0.4% (v/v) sodium hypochlorite solution for 20 min with occasional agitation. The seeds were then rinsed four times with sterile distilled water. Sterilized seeds were germinated on a ½ Murashige and Skoog (MS) basal medium for germination. 0.7-cm-long hypocotyl explants were excised consecutively. Segments of explant were cultured in standardized MS medium supplemented with BAP (1 mg/L) and NAA (1 mg/L). The cultures were incubated under a 16 h photoperiod at 25±2 C. After 4-7 weeks, developed calli were sub-cultured in fresh MS medium (BAP (1 mg/L) and NAA (1 mg/L)) each month.

Experiments with Established Tobacco Cell Culture and Statistical Analysis: Special tubes for the plant cell culture (Phytotechnology Laboratories, Inc.) were used for experiments with established tobacco callus. The basic medium for callus cultivation was the MS medium supplemented with about 1 mg/L 2,4-D, which was used as a control medium. For experimental conditions, the control medium was supplemented with MWCNTs in concentrations of about 0.1, 5, 100, and 500 μg/mL, or with activated carbon (AC) in the same concentrations: 0.1, 5, 100, and 500 μg/mL. An equal amount of initial callus (inoculum), about 300 mg, was placed in each experimental tube containing agar medium with or without carbonaceous material. The experimental tubes were kept in dark conditions at about 22-24° C. in a growth chamber for about 1 month. Each experimental condition was replicated 10 times (10 tubes were used for each concentration of carbon nanotubes, activated carbon, or control medium). All of the experiments were repeated twice; therefore, each data point is the average of 20 individual measurements. Thus, vertical bars indicate ±SE (n=20).

Exposure of *Catharanthus roseus* callus to CBNs: *Catharanthus roseus* callus cultures were maintained on full strength Murashige and Skoog (MS) with vitamins (PhytoTechnology Laboratories, Mission, Kans.), supplemented with 30 g/L sugar, 1 mL/L α-naphthaleneacetic acid (NAA) (PhytoTechnology Laboratories, Mission, Kans.), 1 mL/L 6-benzylaminopurine (BA) (PhytoTechnology Laboratories, Mission, Kans.), and ?0.8 percent agar. Maintenance medium was also used as control medium during experimentation. *Catharanthus roseus* callus was grown on medium containing one of three experimental groups: 50 μg/mL activated carbon (AC), 50 μg/mL CBN, or 100 μg/mL CBN. CBNs tested were long multiwalled carbon nanotubes (MWCNTs) and graphene. Callus inoculum of the same weight (200 mg) were added on top of the medium and incubated either exposed to 70 to 85 μmol s$^{-1}$ m$^{-2}$ light in a 24 h photoperiod (light condition) or covered with foil (dark condition). Total biological replicates for each group numbered 9 (n=9). In summary, 4 experiments were carried out: 2 using MWCNT in light and dark cultivation condition and 2 using graphene in light and dark cultivation condition.

Biomass Measurements: Callus was allowed to grow for a period of 4 weeks. Upon harvest, callus was weighed. The associated data are represented by the mean of the 9 biological replicates. Error bars represent the standard error. Changes in biomass observed in experimental groups compared to control were considered significant if $p<0.05$. Statistical analysis was completed using Microsoft Excel software (Microsoft, Redmond, Wash., USA).

Alkaloid Extraction: Alkaloid extraction was as previously described with small modification (Monforte Gonzalez et al., 1992). Briefly, harvested callus cultures were freeze-dried and powdered under liquid nitrogen in mortar and pestle. 50 mg frozen, powdered *Catharanthus roseus* callus was homogenized in microcentrifuge tubes with 5 mL methanol and shaken for 2 hours at 55° C. Afterwards, 5 mL 2.5% $H_2SO_4$ were added, solution was vortexed and allowed to settle until phase separation was clear, and the aqueous phase was moved to a new tube and washed three times with ethyl acetate. Solution was alkalized with NaOH to a pH above 10, 5 mL ethyl acetate was added, aqueous phase was discarded, and organic phase was dried using a rotovap. Samples were reconstituted in 3 mL methanol.

Bulk Alkaloid Estimation: Reconstituted samples were loaded into quartz cuvettes for analysis in a Varian Cary 5000 dual-beam spectrophotometer at a wavelength of 280 nm. Every sample was measured for three technical replicates and run alongside a methanol blank. Quantification done by the machine was based upon a standard curve of mixed alkaloid standards ($R^2=0.9202$). Alkaloids in the standard mixture were vincristine, vinblastine, vindoline, catharanthine, and loganin. Further statistical analysis was completed in Microsoft Excel software (Microsoft, Redmond, Wash., USA). Changes in total alkaloid content in experimental groups compared to control were considered significant if $p<0.05$. Error bars represent standard error.

Synthesis and Processing of Nanoparticles: High yield and crystalline MWCNTs were synthesized by chemical vapor deposition (CVP) connected to a radio-frequency (RF) generator with about 350 kHz frequency, as previously reported [35-38]. Produced MWCNTs were purified with a diluted hydrochloric acid under continuous agitation [35]. Subsequently, the sample was washed with deionized (DI) water to ensure complete removal of the acid. The cleansed nanotubes were found to have a purity of about 98%, while still remaining free of defects. TEM analysis indicated that the MWCNTs used in this example have average diameter of about 20 nm and lengths between about 500 nm to about 1 μm.

Raman Spectroscopy: The tobacco cells grown for about 1 month on the MS medium supplemented with about 100 μg/ml of the MWCNTs were used for Raman-scattering analysis. The cells that did not have direct contact with MWCNTs containing medium (top of callus) were carefully collected and analyzed. Raman-scattering analysis was performed at room temperature with a Horiba Jobin Yvon LabRam HR800 spectrometer equipped with a charge-coupled detector and two grating systems (600 and 1800 lines/mm). A 633 nm (1.96 eV) laser excitation was used for these studies. The laser beam intensity at the sample surface was about 20 mW and was focused through an Olympus microscope to a spot size of <1 μm². The backscattered light was collected in a 180° geometry from the direction of incidence. Raman shifts were calibrated on a silicon wafer at the 521 cm−1 peak.

Transmission Electron Microscopy (TEM) of Tobacco Cells: Callus samples (upper part of calluses grown on a regular MS medium and calluses grown on the MS medium supplemented with MWCNTs of about 100 μg/mL) were carefully removed from the surface of the agar with a spatula, placed on dental wax, cut into about 1 mm cube blocks with a razor blade, and fixed in 3% glutaraldehyde in 0.075 M Sorensen's buffer, pH 7.2 for about 42 h at about 4° C. Thereafter, the callus pieces were washed three times for about 30 min each in 0.075M Sorensen's buffer, pH 7.2 at about 4° C. Samples were then post-fixed in 1% osmium tetroxide in 0.075 M Sorensen's buffer, pH 7.2 for about 2 h at about 4° C. in the dark. The callus pieces were again washed three times for about 30 min each in 0.075 M Sorensen's buffer, pH 7.2 at about 4° C., followed by dehydration in a graded ethanol series (about 30%, 50%, 70%, 95%, and 3-100%) in 30-min to 1-h increments beginning at about 4° C. and warming to room temperature in 100% ethanol. The callus pieces were infiltrated with Spurr's resin over several days and cured at about 70° C. overnight. Thin sections were cut from the embedded samples using an ultramicrotome equipped with a diamond knife and were mounted on copper grids. The grids were stained with uranyl acetate and lead citrate before examination with a transmission electron microscope (JEOL 1200EX). Images were captured with KODAK 4489 film which was subsequently scanned using an EPSON PERFECTION 4870 photo flatbed scanner at 1200 dpi. Scanned images were processed and labeled using PHOTOSHOP CS4.

Figure 8:
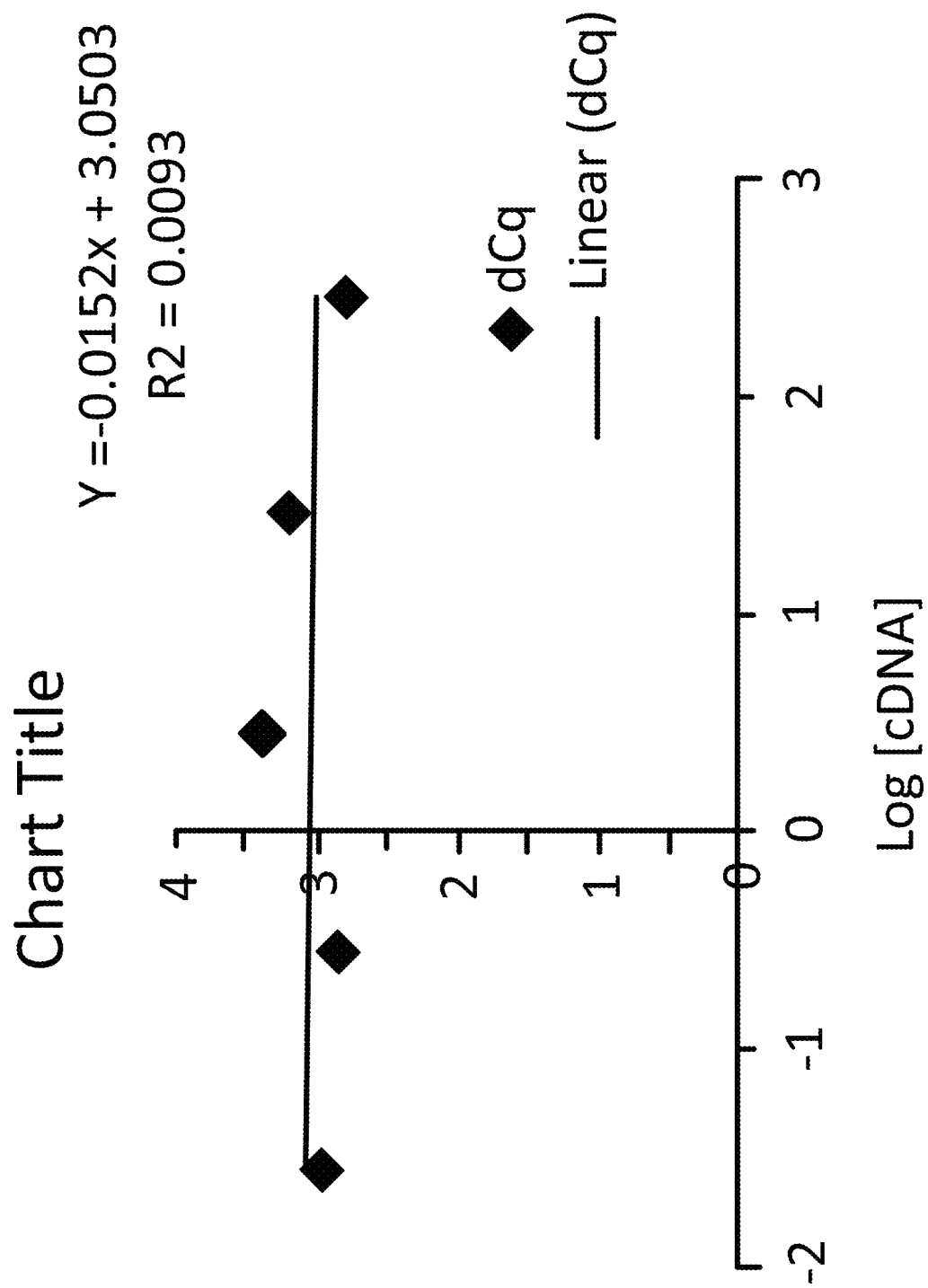
FIG. 8 shows an assessment of tobacco aquaporin gene and actin for equal amplification efficiencies.

Real-Time PCR Analysis: Total RNA samples from tobacco cells incubated on the regular MS medium, the MS medium supplemented with MWCNTs (100 ug/ml), or the MS medium supplemented with activated carbon (100 ug/ml) at the initial stage of incubation (0 days) and at different time points of incubation (6 hours, 24 hours, 4 days, 8 days, 16 days, 25 days) were isolated using RNeasy Plant Mini Kit (Qiagen Inc. Valencia, Calif.). Residual DNA was removed by on-column DNA digestion using the RNase-free DNase Kit (Qiagen Inc. Valencia, Calif.). Synthesis of cDNA was carried out using SuperScript III First Strand Synthesis System Kit (Invitrogen, Carlsbad, Calif.) with dT16-oligonucleotide primers according to the manufacturer's protocol. NtLRX1 (extensin1) gene (AB273719) was amplified using 5'-AGCCACCACCATACACACCT-CAAT-3' (forward primer) and 5'-TGGTGGTGAA-GACGGTGTCACATA-3' (reverse primer); NtPIP1 (AF440271) gene was amplified using 5'-GGTTCAT-TTGGCCACCATCCCAAT-3' (forward primer) and 5'-GCAGCAAGAGCAGCTCCAATGAAT-3' (reverse primer); CycB gene (AY776171) was amplified using 5'-TTCTGGCTGAGCTGGGATTGATGA-3' (forward primer) and 5'-TGATGGTGTGTCGAGCAGCATAGA-3' (reverse primer); actin gene (AB158612) as the internal control was amplified using 5'-GAACGGGAAAT-TGTCCGCGATGTT-3' (forward primer) and 5'-ATGGTAATGACCTGCCCATCTGGT-3' (reverse primer). The quantification of expression of all tested genes during 25 days of cell incubation was done by real-time quantitative RT-PCR analysis (qRT-PCR) using SYBR GREEN PCR master mix (Applied Biosystems, Carlsbad, Calif.) in an iCycler iQ Multi Color Real Time PCR detection system (Bio-Rad, Hercules, Calif.). Three independent biological replicates were used in the analysis. The real-time PCR data were generated and analyzed by the "comparative count" method to obtain the relative mRNA expression of each tissue as described in the iCycler manual (Bio-Rad, Hercules, Calif.). Actin was chosen as an internal control based on the equal amplification efficiencies of actin and all analyzed genes (CycB, NtLRX1, NtPIP1). The amplification efficiencies of actin and gene of aquaporin (NtPIP1) are shown in FIG. 8.

Immunoblot Analysis: For analysis of the production of tobacco water channel (aquaporin) protein PIP1, the total protein was extracted from cells incubated on the regular MS medium, the MS medium supplemented with MWCNTs (100 μg/ml), or the MS medium supplemented with activated carbon (100 μg/ml) at the initial stage of incubation (0 days) and at different time points of incubation (6 hours, 24 hours, 4 days, 8 days, 16 days, 25 days) using Plant Total Protein Extraction Kit (Sigma-Aldrich, Inc. St. Louis, Mo.). The analysis of the production of aquaporin protein in tobacco cells was performed using anti-peptide antibodies provided by Pacific Immunology, Inc. (Ramona, Calif.). Antibodies were designed and produced against tobacco aquaporin peptide sequence DAKRNARDSHV. Standard techniques for Western blot analysis [39, 40] were used for the detection of tobacco water channel protein (NtPIP1) in tobacco cells exposed and unexposed to carbonaceous materials. Briefly, for each time point, about 20 μg of total protein were separated by SDS-PAGE followed by Western blot analysis using affinity purified anti-PIP1 primary and anti-rabbit IgG HRP secondary antibodies. Equal loading of the protein was assessed using antiactin primary and antimouse IgG HRP secondary antibodies.

HPLC Quantification of Vinblastine and Vincristine: High-performance liquid chromatography (HPLC) was performed using a Thermo Scientific UltiMate 3000 instrument with Chromeleon software (ThermoFisher Scientific, Fremont, Calif.). (See also [41].) Chromatographic separations were achieved with a Grace C-18 reverse phase column (Grace Davison Discovery Sciences, USA) at 220 nm using a 15 μL injection and the following gradient: 0-29 minutes—45% B, 29-30 minutes—35% B. Solvent A was 0.5% formic acid in HPLC-grade water (Alfa Aesar, Ward Hill, Mass., USA). Solvent B was 100% HPLC-grade methanol (JT Baker, Center Valley, Pa., USA). Flow rate was set to 0.5 mL/min and column oven to 30° C. Chromeleon software (ThermoFisher Scientific, Fremont, Calif.) automatically calculated vincristine and vinblastine concentration in samples based upon standard concentrations of the aforementioned compounds in methanol. Three biological replicates for each sample group were run. Data were exported to Microsoft Excel and VassarStats for statistical analysis (Microsoft, Redmond, Wash., USA). Changes in concentration of either vincristine or vinblastine in experimental groups compared to control were considered significant if $p<0.05$. Error bars represent standard error.

Results and Discussion

To further understand the effects induced by carbon nanotubes on plant cell division/cell growth, culture undifferentiated tobacco cells (callus culture) were exposed to MWCNTs and activated carbon (AC) dispersed into the standard plant cell growth medium (MS supplemented with auxin 2,4-D) in a wide range of concentrations in the exemplary embodiment.

Figure 2:
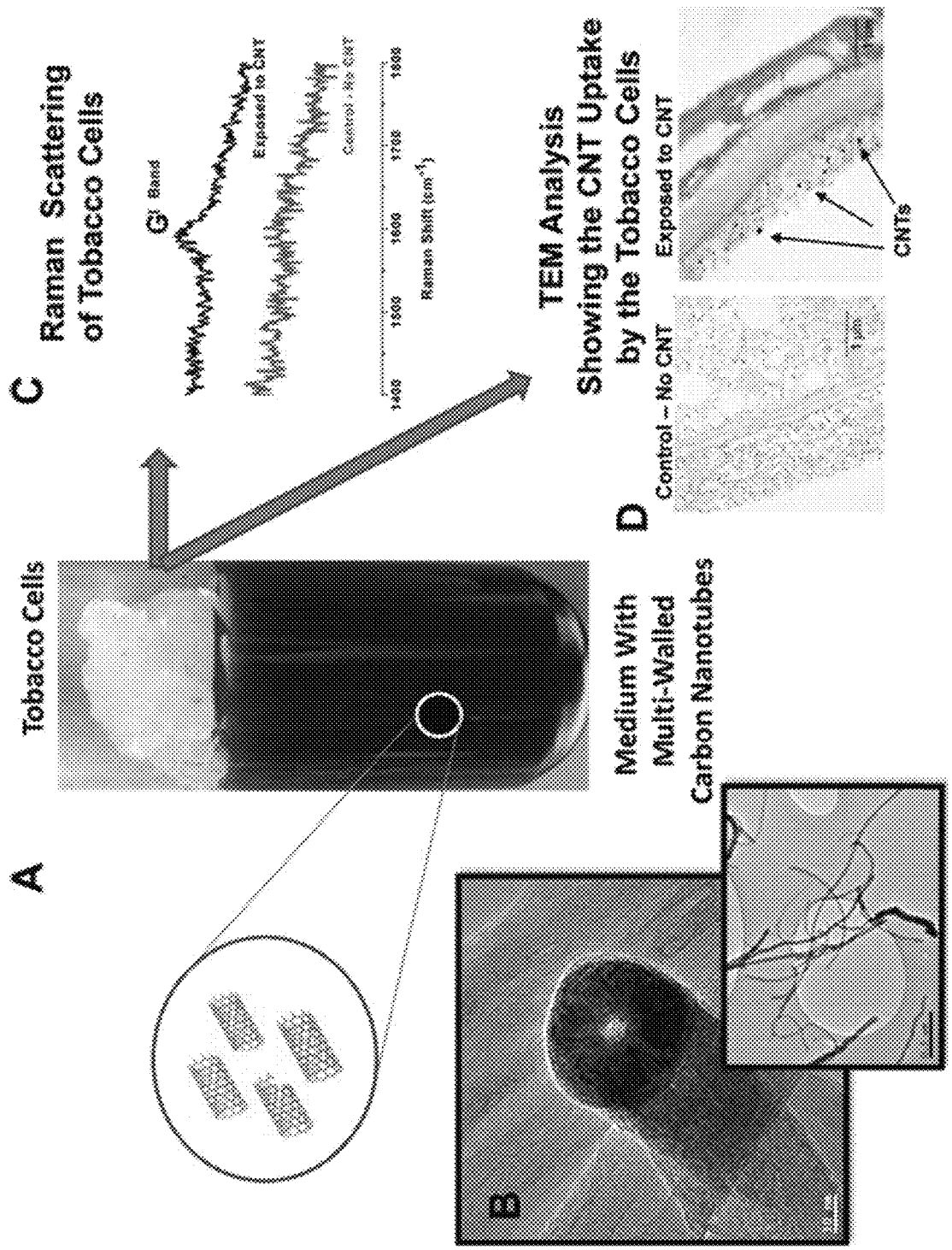
FIG. 2 shows detections of MWCNTs in tobacco cells grown on medium supplemented with MWCNTs according to certain embodiments of the disclosure. (A) Growth of tobacco cells on medium supplemented with 100 µg/mL of MWCNTs. (B) Representative transmission electron microscopy (TEM) image of the nanotubes used in this study. Nanotubes had an average diameter of 20 nm and lengths ranging from 500 nm to 1 µm. (C) Raman analysis of the cells exposed to the MWCNTs indicating that the tobacco plant cells uptake the nanotubes (based on the nanotube-specific 1581 $cm^{-1}$-G band). (D) TEM images of the tobacco cells exposed and unexposed to MWCNTs.

Detection of MWCNTs in Tobacco Cells Grown on Medium Supplemented with MWCNTs: The interaction between MWCNTs and the tobacco cells grown on the MS medium supplemented with MWCNTs was probed with Raman spectroscopy and additionally by TEM, as shown in FIG. 2. The nanotubes' specific G band intensity (the most intense) was analyzed when the samples were exposed to a 633 nm laser excitation. The G band corresponds to the sp2-stretching modes both in ring and chains for the graphitic structures and represents the E2g mode at the center of the Brillouin zone [14, 15]. The presence and relative intensity of the G band (1581 cm$^{-1}$) was associated with the existence of the MWCNTs [16] in the cell samples, as shown in FIG. 2C. The Raman analysis did not indicate any similar peak in the spectra of the control samples not exposed to the MWCNTs. This experimental finding is in good correlation with data that Liu et al. have presented previously and who demonstrated by confocal microscopy that carbon nanotubes have the ability to penetrate the walls of the tobacco cells [7]. It should be mentioned that most of the spectroscopic analytical techniques, such as Raman scattering, lack the ability to very accurately quantify/comparatively assess the amount of nanotubes present inside the cells, but rather can be used to prove the presence of nanotubes in the samples. To additionally show the uptake of the MWCNTs by the tobacco cells, TEM analysis for the grown cells was performed on agar medium with and without the MWCNTs. As shown in FIG. 2D, TEM images clearly showed the presence of clustered nanotubes inside tobacco cells grown on the medium supplemented with the MWCNTs (about 100 μg/mL). It is interesting that the MWCNTs were detected inside the cells that were collected from the upper part of the callus biomass, which did not have any direct contact with the medium. During many rounds of cell division, cell biomass increased significantly. As a result, the cells used for the TEM transfer were most probably never directly exposed to the MWCNTs present in the medium. Therefore, as the cells divided, they move the nanotubes from one generation to the next. Furthermore, the presence of the MWCNTs even in the upper cells indicates that the MWCNTs were uptaken in a significant amount by the initial cell populations that had been in contact with the MWCNTs-supplemented medium. On the basis of these findings, it is expected that the interactions between carbon nanotubes and tobacco cells and the uptake of MWCNTs by cells have the potential to induce significant responses at the cellular and genetic levels.

Figure 3:
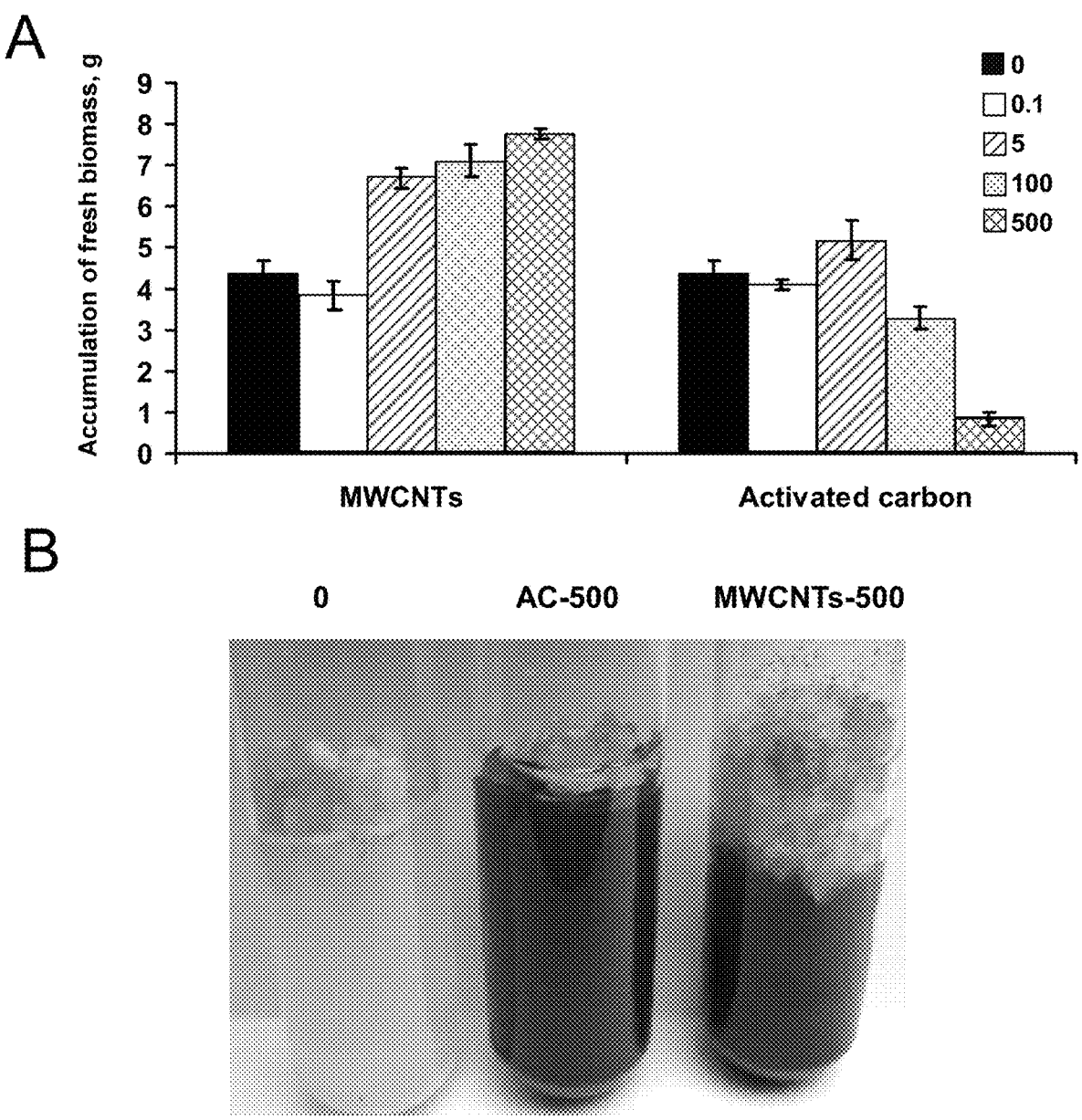
FIG. 3 shows an effect of multi-walled carbon nanotubes (MWCNTs) and activated carbon on growth of tobacco cell culture according to certain embodiments of the disclosure. (A) Biomass accumulation of culture of tobacco cells grown on regular MS medium, MS medium supplemented with activated carbon (0.1, 5, 100, and 500 µg/mL), and MS medium supplemented with MWCNTs (0.1, 5, 100, and 500 µg/mL). (B) Differences in growth of control cells (0) and cells exposed to activated carbon (AC) or multi-walled carbon nanotubes (MWCNTs) in highest tested dose (500 µg/mL). Equal amount of biological material (300 mg) was used for all experimental conditions and all replicates. Each experimental condition was replicated 10 times (10 tubes were used for each concentration of carbon nanotubes, activated carbon, or control medium). The entire experiment was repeated twice. Thus, vertical bars indicate ±SE (n=20).
Figure 4:
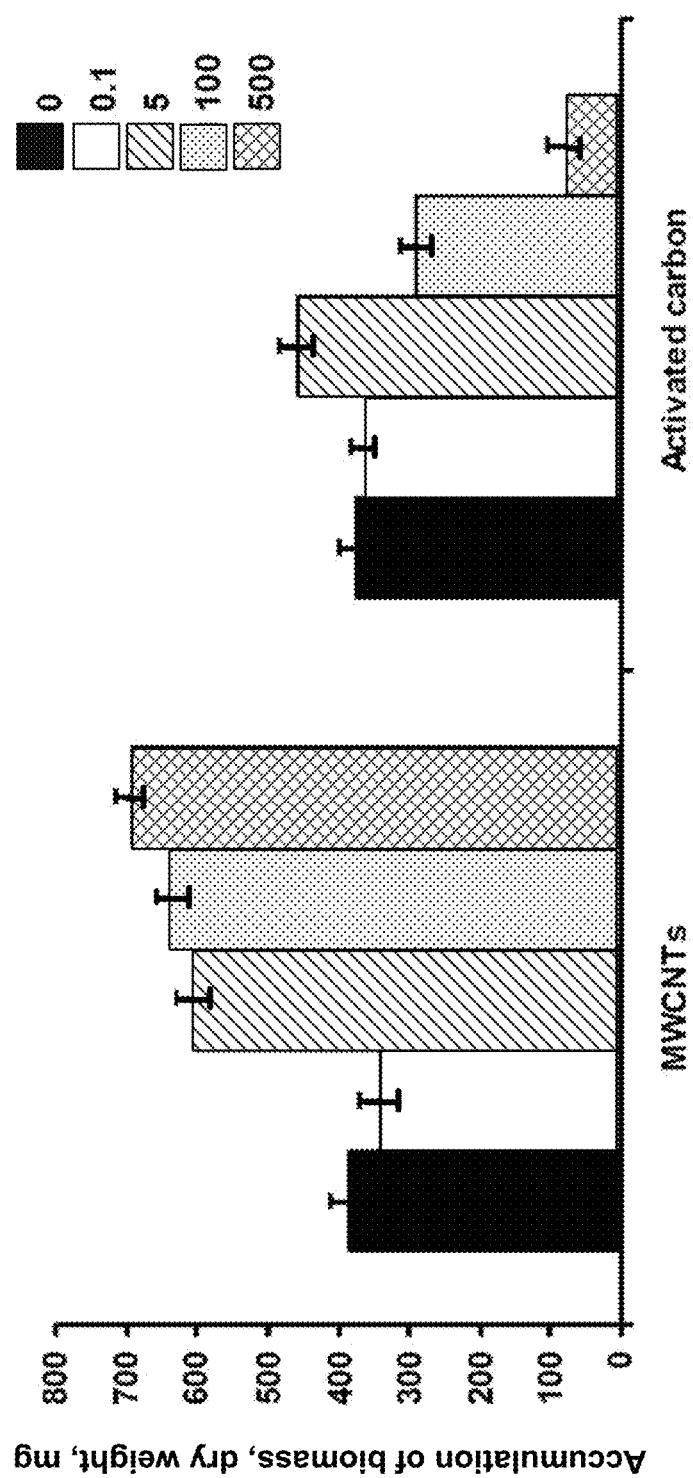
FIG. 4 shows total dry weight of tobacco callus grown on control MS medium and medium supplemented with carbonaceous materials according to certain embodiments of the disclosure. Each experimental condition was replicated 10 times (10 tubes were used for each concentration of carbon nanotubes, activated carbon or control medium). The entire experiment was repeated twice. Thus, vertical bars indicate ±SE (n=20).

Activation of Growth of Tobacco Cell Culture in the Presence of MWCNTs: To understand how different concentrations of the MWCNTs would affect cell division in callus culture, the total accumulation of cell biomass (fresh weight and dry weight) was measured after 1 month of cell incubation with and without MWCNTs or with activated carbon. To standardize the weight-measuring experiments among the various experimental replicates (20 times for each treatment), tubes specifically designed for plant tissue culture, as previously shown in the studies [17, 18], were used. As presented in FIG. 3A, both MWCNTs and AC affected tobacco cell growth. MWCNTs enhanced cell growth by 55% to 64% for the concentration range of 5-500 μg/mL. A more modest activation of cell growth (16% increase) was observed for the cells exposed to AC at low concentrations (5 μg/mL), while a significant decrease in cell growth was observed for high doses (100 and 500 μg/mL). The average dry weight of biomasses accumulated under each experimental condition was measured as well. It was found that the dry weight of calluses was in direct correspondence with the fresh weight and represented 9% of the total fresh weight in all of the experimental conditions that were investigated. The total dry weight of tobacco callus grown on the control MS medium and the MS medium supplemented with carbonaceous materials are shown in FIG. 4. Each experimental condition was replicated 10 times (10 tubes were used for each concentration of carbon nanotubes, activated carbon or control medium). The entire experiment was repeated 2 times. Thus, vertical bars indicate ±SE (n=20).

According to the disclosure, the addition of the MWCNTs to the medium resulted in an increase in both the fresh and dry weight of the calluses. This observation is an indication that an increase in cell growth is associated with the activation of cell division and not associated with an increase in a cell volume through the enhancement of water uptake. The modest (16%) activation of growth in the cells exposed to the AC (about 5 μg/mL) could be explained by the ability of activated carbon to adsorb substances presumed to be deleterious or inhibitory to callus growth during long-term cultivation [19]. The inhibition of callus growth in the medium supplemented with AC in higher doses (about 100 and 500 μg/mL) could be associated with the non-selective ability of the AC to adsorb substances from the MS growth medium, including plant growth regulators, vitamins, iron chelate, and Zn [20].

It is important to emphasize that, according to embodiments of the disclosure, the MWCNTs in a high concentration (about 500 μg/mL) were not found to be toxic to cells, but were instead able to stimulate cell growth, as shown in FIG. 3B. The findings highlights the positive effects of the MWCNTs on tobacco cells, although this topic is still under intense scientific investigation, since several studies have reported contradictory results [21, 22]. Earlier, various aspects describing the toxicity of multi-walled carbon nanotube agglomerates were reported for Arabidopsis [21] and rice [22] suspension cell cultures. One possible explanation for such results is related to the exact plant systems used for the investigations, as well as the conditions under which the nanotubes were delivered and their co-chemical characteristics. If the nanostructures agglomerate, their behavior could differ drastically from that observed when they are individually dispersed. Such contradictions in the cells' physiological responses to nanostructural materials may be further explained by the differences in the specific characteristics of the nanotubes used during the experiment (size, level of agglomeration, and distribution in a growth medium), the duration of the incubation of cells with nano-sized materials, the concentrations of carbon nanotubes, and the type of medium used for cultivation (solid or liquid), as well as the type and age of the plant material. Recently, the inventors have demonstrated the need for a thorough understanding of the complex bioactivity of each component of a nanoscaled system that is introduced to plant models, since each of these components could induce its own individual toxicity [23]. Particularly, in the case, the attachment of quantum dots (QD) to carbon nanotubes completely reversed the positive physiological responses that were recorded for the tomato plants exposed to carbon nanotubes only. Tomato plants grown on medium supplemented with QD-CNT aggregates exhibited symptoms of early leaf senescence and inhibition of root growth, which were not observed for the plants exposed to MWCNTs only. Moreover, the inventors have clearly shown that even the morphology/shape of the graphitic nano-sized materials (single-walled or multi-walled carbon nanotubes and graphene layers) can induce different physiological responses in tomato plants [13].

Figure 5:
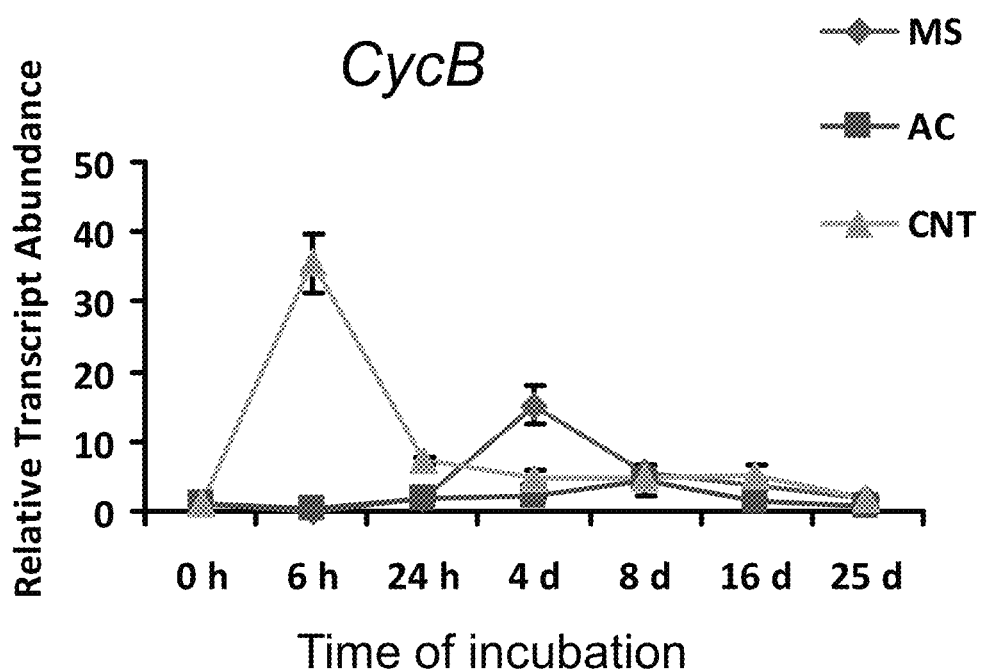
FIG. 5 shows relative transcript abundance of CycB (A) and NtLRX1 (B) genes in tobacco cells cultured on standard medium (MS), MS medium supplemented with 100 µg/mL of MWCNTs (CNT), or supplemented with 100 µg/mL of activated carbon (AC), according to certain embodiments of the disclosure. Expression of genes was analyzed by real-time PCR. Results are shown as the average of three independent biological replicates. Relative expression levels were normalized to an internal standard (actin) for each treatment. Bars represent the standard error (SE).
Figure 5:
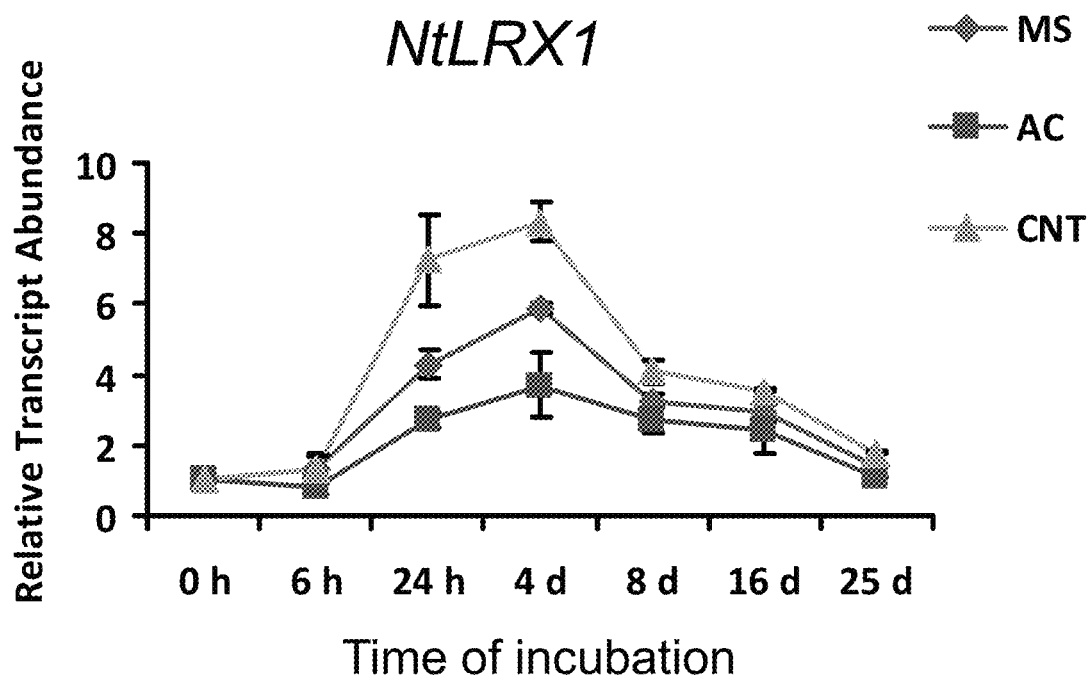

Expression of Genes Involved in Cell Division and Extension Affected by Carbon Nanotubes: The observations according to embodiments of the disclosure, as shown in FIG. 3, suggest the existence of different molecular mechanisms for cell growth activation by the nano-sized MWCNTs and by the AC. To test this hypothesis, the expressions of genes essential for cell-wall assembly/cell growth, such as extensin (NtLRX1), and for the regulation of cell cycle progression, CycB, in tobacco cells grown on the medium supplemented with 100 µg/mL of MWCNTs or AC, as well as on the regular MS medium (control) were monitored. Using the real-time PCR analysis, it was found that both genes exhibited the highest level of expression when the cells were treated with MWCNTs, as shown in FIGS. 5A and 5B. The expression of the CycB gene was significantly elevated in the MWCNT-treated tobacco cells, increasing by a 35-fold after only about 6 h of cell incubation. A 15-fold increase in the expression of the CycB gene was detected on the fourth day of incubation in control (untreated) cells, whereas the lowest expression of the CycB gene was found in the cells treated with activated carbon, as shown in FIG. 5A. Thus, the transcription of the cell cycle regulator CycB can be significantly and rapidly induced by the MWCNTs in tobacco cells. Earlier, Schnittger et al. experimentally proved that ectopic CycB1;2 expression is important for plant cell division and demonstrated that it can induce nuclear divisions and is sufficient to switch between endoreduplication and mitosis in Arabidopsis trichomes [24]. The expression analysis of the tobacco CycB gene, as shown in FIG. 5A, is correlated with the observed enhanced growth of the cells exposed to the MWCNTs (100 µg/mL) as compared to those exposed to the AC (100 µg/mL), or the control samples, as shown in FIG. 3. Furthermore, the expression of the NtLRX1 gene (extensin1) was also monitored, which plays a key role in cell wall reinforcement during plant development and in response to external signals [25, 26].

According to the exemplary embodiments of the disclosure, significant changes in the transcript abundance of the NtLRX1 gene between the control, MWCNTs-exposed, and AC-exposed cells, during up to 25 days of incubation were recorded. The highest expression of NtLRX1 was detected in cells incubated on the medium supplemented with the MWCNTs (100 g/mL) between 1 and 4 days of exposure, as shown in FIG. 5B. The NtLRX1 expression was lower for the cells exposed to the AC (100 µg/mL) and in control cells (2.5 fold and 1.5 fold, respectively). There is experimental evidence that plant extensins are synthesized in cells in response to physical damage or environmental stress conditions including wounding [27, 28].

The data suggest that nano-sized carbon materials (e.g., MWCNTs) can be sensed by cells in a manner similar to an environmental stress. Therefore, it is possible that the overexpression of NtLRX1 (extensin 1) has contributed to the observed enhancement in the tobacco cell growth by the MWCNTs. Previously, Bucher et al. demonstrated a direct correlation between the expression of LeExt1 gene encoding tomato extensin-like protein and cellular tip growth [28].

Figure 6:
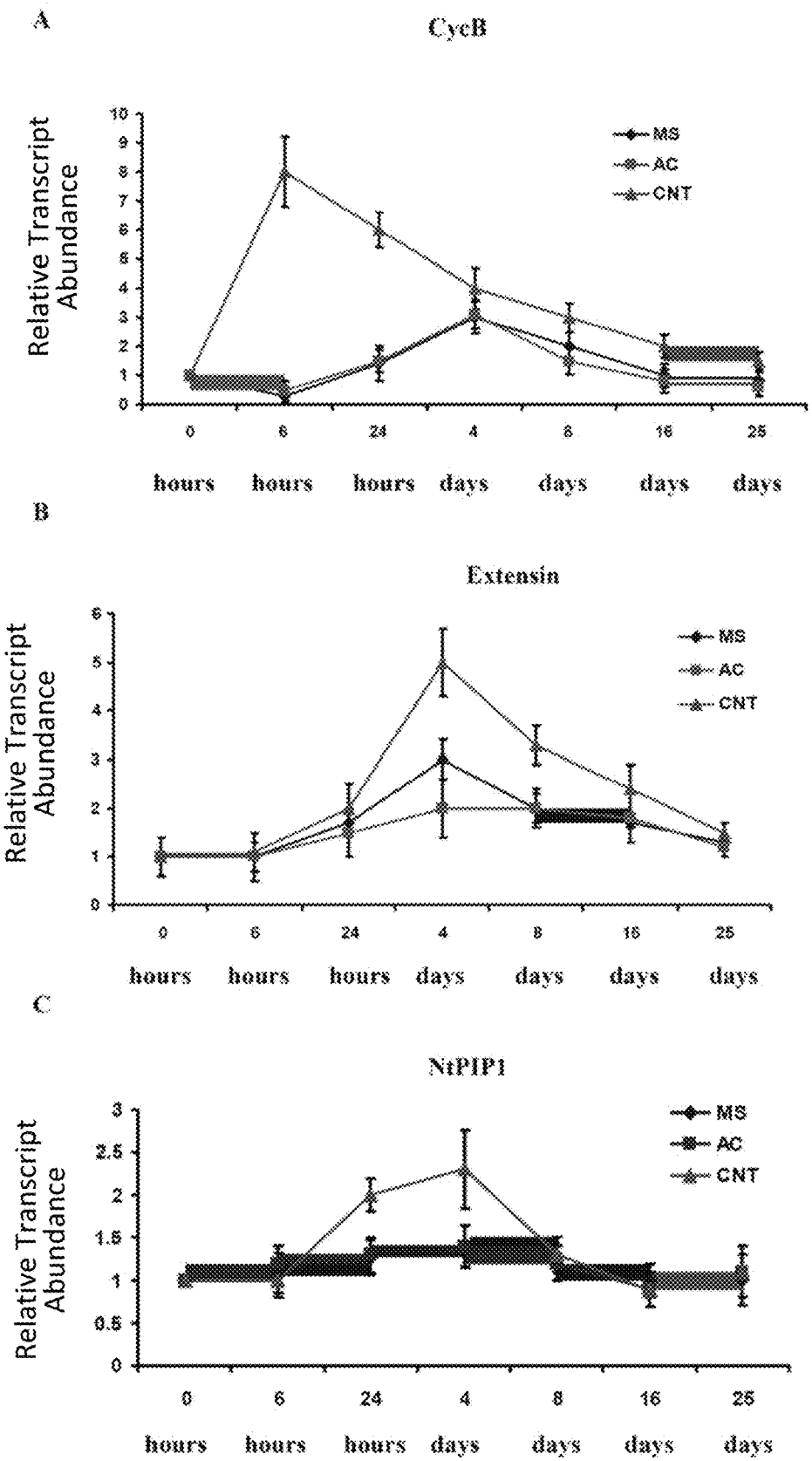
FIG. 6 shows relative transcript abundance of CycB (A) and NtLRX1 (B) and PIP1 (C) genes in tobacco cells cultured on standard medium (MS), MS medium supplemented with 5 µg/ml of MWCNTs (CNT), or supplemented with 5 µg/ml of activated carbon (AC) according to certain embodiments of the disclosure. Expression of genes was analyzed by real-time PCR. Results are shown as the average of three independent biological replicates. Relative expression levels were normalized to an internal standard (actin) for each treatment. Bars represent the standard error (SE).

Additionally, the expressions of both tested genes (NtLRX1 and CycB) in the grown cells on the medium supplemented with very small amounts of the MWCNTs or the AC (5 µg/mL) were also monitored. No differences between the expressions of both genes in the control cells and the cells exposed to a low amount of the AC were found. However, the expressions of NtLRX1 and CycB were activated in the cells exposed to a small amount of the MWCNTs compared with the control and AC-exposed cells. Relative transcript abundance of CycB and NtLRX1 and PIP1 genes in tobacco cells cultured on a standard medium (MS), an MS medium supplemented with 5 µg/ml of the MWCNTs, or an MS medium supplemented with 5 µg/ml of the AC are shown respectively in FIGS. 6A-6C. The expressions of genes were analyzed by the real-time PCR. Results were shown as the average of three independent biological replicates. Relative expression levels were normalized to an internal standard (actin) for each treatment. Bars in the expressions of genes in FIGS. 6A-6C represent the standard error (SE). This observation supported the suggestion that molecular mechanisms for the cell growth activation by the MWCNTs and by the AC are indeed different.

Figure 7:
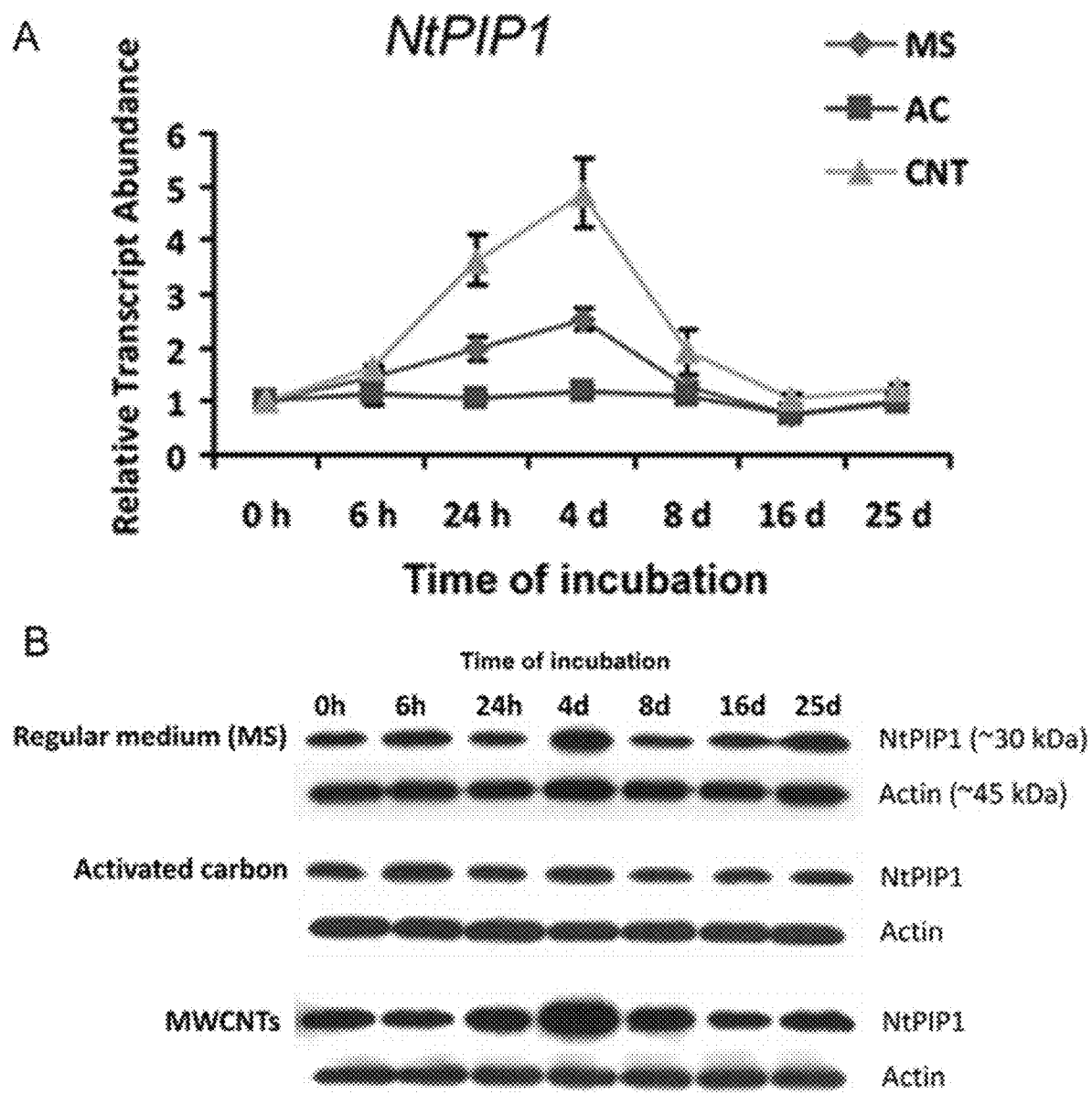
FIG. 7 shows an analysis of the expression of tobacco aquaporin gene (NtPIP1) by real-time PCR (A) and of NtPIP1 protein by Western blot (B) during 25 days of incubation of cells grown on standard MS medium (MS), MS medium supplemented with 100 µg/mL of MWCNTs (CNT), or supplemented with 100 µg/mL of activated carbon (AC). Results of real-time PCR are shown as the average of three independent biological replicates. Actin was chosen as an internal control based on equal amplification efficiencies of actin and analyzed genes. Amplification efficiencies of actin and aquaporin are shown in FIG. 8. The relative expression levels were normalized to an internal standard (actin) for each treatment. Bars represent the standard error (SE). Western blot was repeated four times. Equal loading of the protein was assessed using anti-actin primary and anti-mouse IgG HRP secondary antibodies.

Regulation of Tobacco Water Channels (Aquaporins) in the Presence of Carbon Nanotubes: Moreover, the findings according to the embodiments of the disclosure also suggest that carbon nanotubes have multifaceted effects on plant transcriptome and can affect the expression of a number of genes that are essential for cellular functions. This assumption was further proved by analyzing the effect of the MWCNTs on the expression of the water channel gene (NtPIP1) and production of corresponding NtPIP1 protein in tobacco cells, as show in FIG. 7. Significant up-regulation of the NtPIP1 gene was detected by the real-time PCR analysis in the cells exposed to the MWCNTs (100 µg/ml), from 24 hours to 4 days of incubation, whereas the level of the NtPIP1 expression did not change for the cells grown on the medium supplemented with the AC (100 µg/ml). Additionally, the production of NtPIP1 protein during 25 days of the cell incubation was monitored using Western blot analysis, as shown in FIG. 7B. Consistent with the gene expression data shown in FIG. 7A, the production of NtPIP1 protein reached a maximum on the 4th day of exposure to the MWCNTs (100 µg/ml) and was higher than in the unexposed cells or those cells treated with the AC (100 µg/ml). Equal loading of the protein samples was assessed using antibodies raised against actin protein as shown in FIG. 7B. There are reports indicating that water channel proteins (aquaporins) are central components in plant-water relations and are crucial for root water uptake, seed germination, cell elongation, reproduction, and photosynthesis [29,30]. It has been shown that overexpression of Arabidopsis plasma membrane water channel gene (PIP1b) in tobacco plants leads to an increase in plant growth rate, transpiration rate, stomatal density, and photosynthetic efficiency [31]. The authors concluded that symplastic water transport via water channels represents a limiting factor for plant growth. Similarly, Sade et al. demonstrated that the constitutive expression of the SLTIP2;2 gene (tomato aquaporin) resulted in an increase in the osmotic water permeability of the cells and that transgenic plants transpired more and for longer periods under drought stress compared to control plants [32]. SLTIP2;2 expressing plants showed an increase in fruit yield, harvest index, and plant biomass by comparison with control tomato plants. It was shown also that the overexpression of aquaporin genes (OsPIP1;3) in seed embryos of rice promoted seed germination under water-stress conditions [33]. The data according to embodiments of the disclosure provide the first evidence that carbon nanotubes are able to enhance the production of water channel protein, which may regulate cell growth.

Effect of CBN Exposure on Total Alkaloid Accumulation in *Catharanthus* Callus

Figure 9:
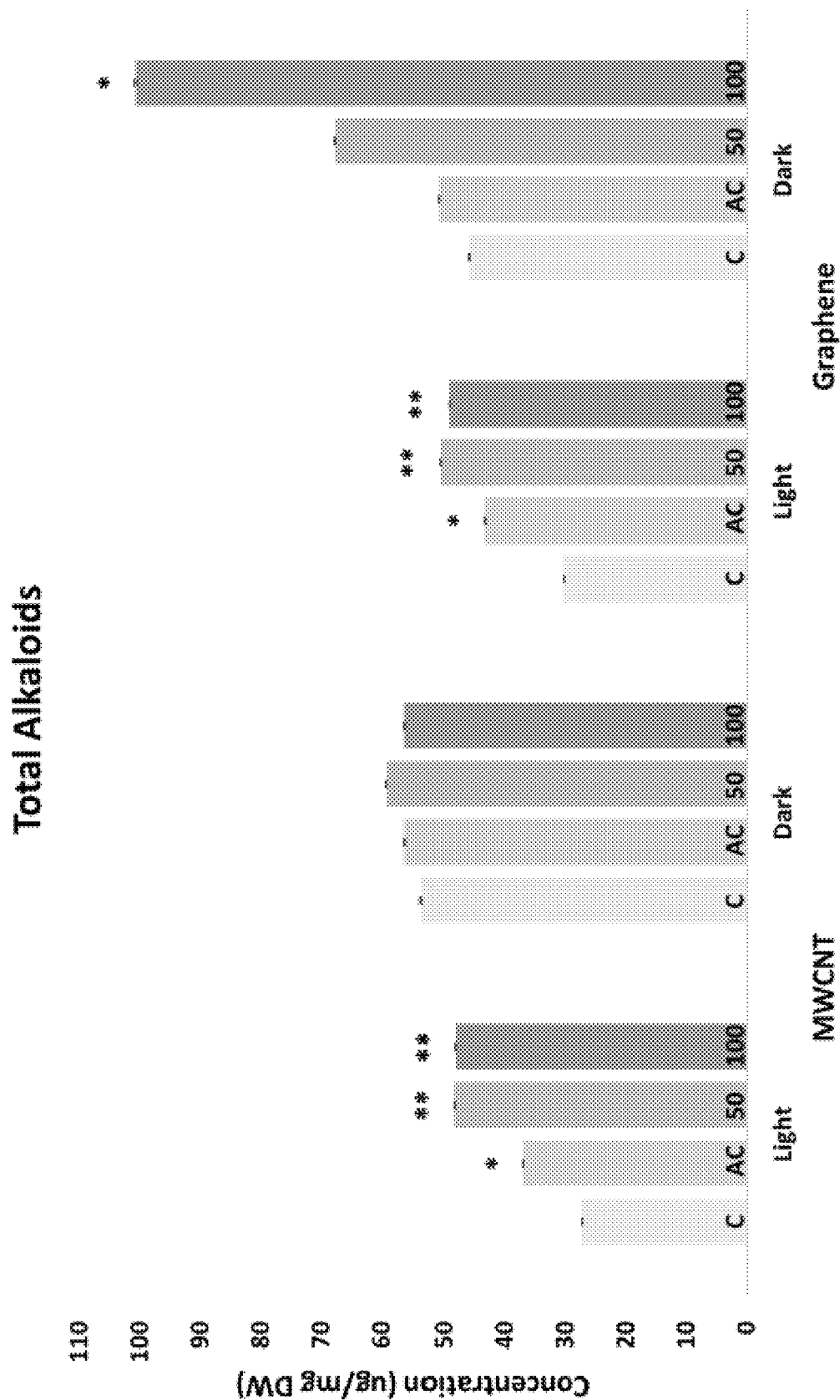
FIG. 9 shows the effect of carbon-based nanomaterial (CBN) exposure on total alkaloid content in callus cultures of *Catharanthus roseus* after 4 weeks of culture. Inocula of 200 mg were grown in the presence of light or in the dark. Experimental groups included control (C) with no CBNs, activated carbon (AC), 50 µg/mL CBN (50), and 100 µg/mL CBN (100). CBNs tested were multiwalled carbon nanotubes (MWCNT) and graphene. Concentration of total alkaloids is represented as average µg of alkaloid per mg of *Catharanthus roseus* callus dry weight or 9 biological replicates. $*p<0.05$, $**p<0.01$. Error bars represent standard error values.

*Catharanthus* is capable of producing more than 100 alkaloids, many of which have pharmaceutical properties [34]. To investigate the effect of CBN exposure on the total alkaloid accumulation in cell cultures of *Catharanthus roseus*, we coupled an alkaloid extraction method with a spectrophotometric (HPLC) analysis. As seen in FIG. 9, MWCNT exposure via medium was only able to significantly affect alkaloid concentrations of *Catharanthus roseus* callus cultures when they were grown in the light condition. When *Catharanthus roseus* callus was grown in the light cultivation condition, 50 μg/mL MWCNT in the medium increased the total alkaloid content of the callus cultures by 77.5% (p=0.00289). 100 μg/mL MWCNT in the same condition increased total alkaloid content of *Catharanthus roseus* callus by 76.7% (p=0.00289). Inclusion of 50 μg/mL graphene in the medium increased the total alkaloid concentration of *Catharanthus roseus* callus by 66.9% (p=0.0101) when callus was grown in the light condition. The same concentration of graphene did not significantly affect total alkaloid concentration when *Catharanthus roseus* callus was grown in the dark cultivation condition. Inclusion of 100 μg/mL graphene in the medium increased the total alkaloid concentration of *Catharanthus roseus* callus by 62.4% (p=0.0102) when callus was grown in the light condition. In the dark cultivation condition, inclusion of 100 μg/mL graphene in the medium did increase total alkaloid concentration of *Catharanthus roseus* callus by 54.4% (p=0.0299). The presence of activated carbon in the media increased the total alkaloid concentration of *Catharanthus roseus* callus by 35.7% (p=0.0477, MWCNT experiment) and 42.7% (p=0.0307, graphene experiment) when callus cultures were grown in the light condition. Activated carbon did not significantly increase the total alkaloid concentration of *Catharanthus roseus* callus when cultures were grown in the dark condition. Inclusion of MWCNT in the medium did not significantly increase the total alkaloid concentration of *Catharanthus roseus* callus when cultures were grown in the dark cultivation condition, so this experiment was not further analyzed by high-performance liquid chromatography (HPLC).

Figure 10:
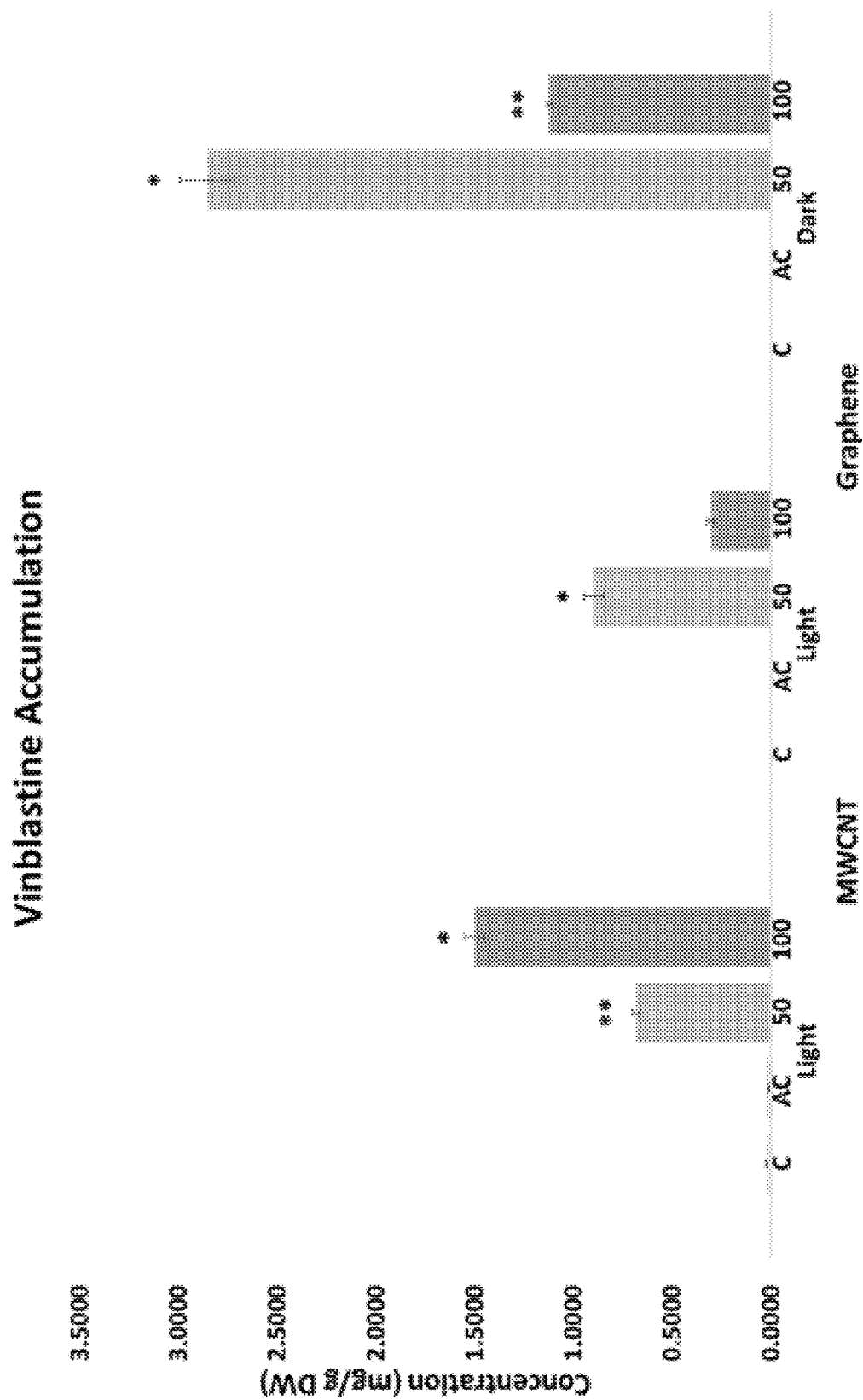
FIG. 10 shows the concentration of vinblastine in *Catharanthus roseus* callus cultures after 4 weeks of cultivation on media containing no carbon-based nanomaterials (control, C), activated carbon (AC), 50 µg/mL CBN (50), or 100 µg/mL CBN (100). Callus cultures were grown in the presence of light or in the dark. CBNs tested were multiwalled carbon nanotubes (MWCNT) and graphene. Concentration is the average of three biological replicates presented as the average mg of vinblastine per g dry weight (DW). $*p<0.05$, $**p<0.01$. Error bars represent standard error values.

Effect of CBN exposure on vinblastine accumulation in *Catharanthus roseus* callus: Vinblastine is an alkaloid produced by *Catharanthus roseus* and used to treat cancers like breast cancer, choriocarcinoma, Hodgkin lymphoma, and more. We have used HPLC analysis to investigate the effect of CBN exposure on the accumulations of vinblastine in callus cultures of *Catharanthus roseus*, as seen in FIG. 10. When *Catharanthus roseus* callus was grown in the dark cultivation condition, vinblastine was not present at detectable levels in control samples. Both concentrations of graphene (50 μg/mL and 100 μg/mL) significantly increased the concentration of vinblastine in *Catharanthus roseus* when callus was grown in the dark cultivation condition. 50 μg/mL graphene exposure of *Catharanthus roseus* increased vinblastine from an undetectable level in control samples to 2.8516 mg/g dry weight (DW) (p<0.05). 100 μg/mL graphene in the medium increased vinblastine concentration from an undetectable level in the control group to 1.1219 mg/g DW (p<0.01). Inclusion of graphene in medium of *Catharanthus roseus* callus grown in the light condition only significantly affect vinblastine concentration when a concentration of 50 μg/mL was used. This concentration increased vinblastine concentration from an undetectable level in the control group to 0.8949 mg/g DW (p<0.05). Both concentrations of MWCNT significantly affected vinblastine concentration in *Catharanthus roseus* callus cultures when they were grown in the light condition. A concentration of 50 μg/mL MWCNT increased vinblastine concentration by 0.6588 mg/g DW (p<0.01), whereas a concentration of 100 μg/mL increased vinblastine concentration by 1.4778 mg/g DW (p<0.05). Activated carbon exposure did not significantly affect vinblastine concentration in either experiment.

Figure 11:
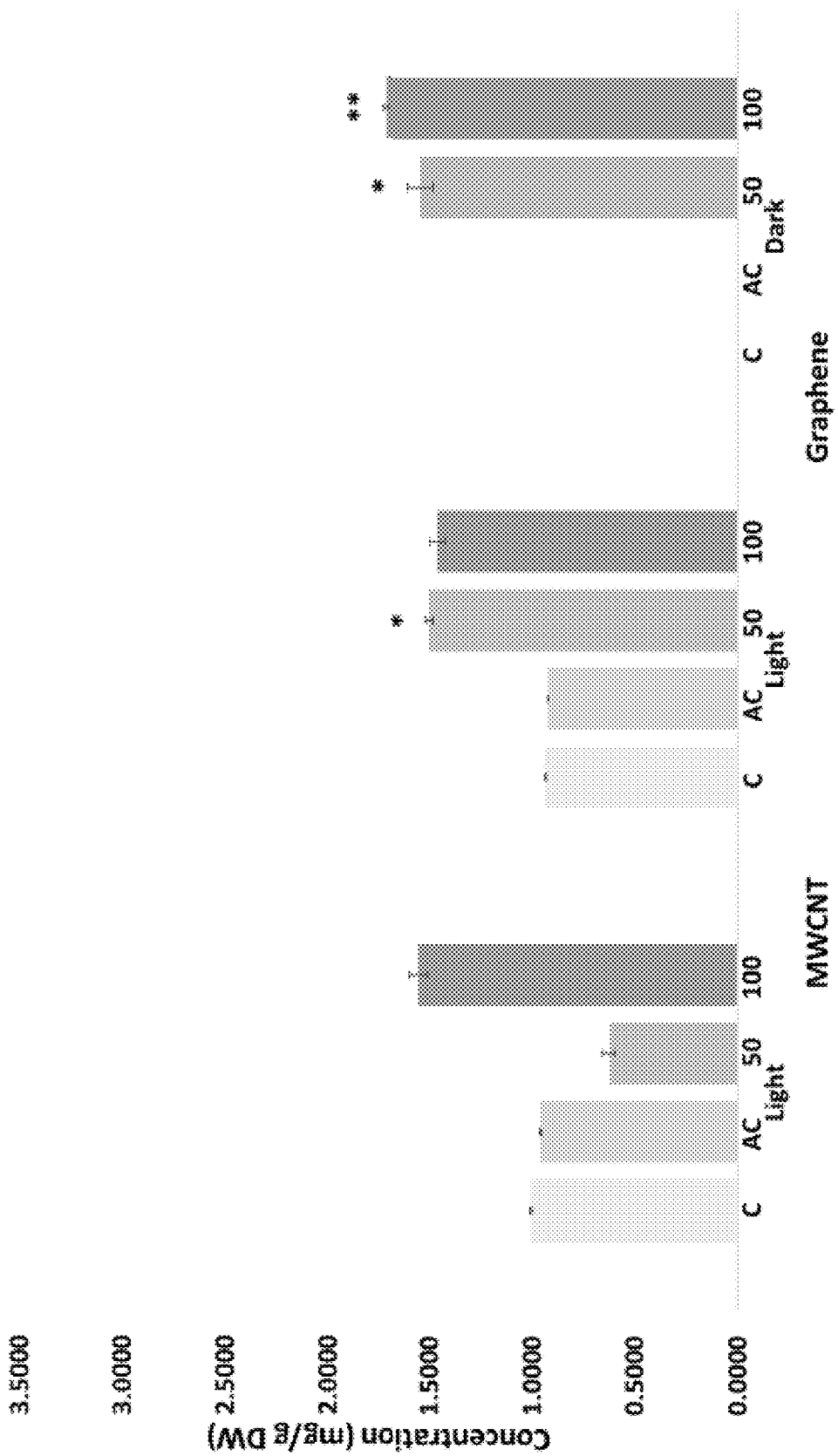
FIG. 11 shows the concentration of vincristine in *Catharanthus roseus* callus cultures after 4 weeks of cultivation on media containing no carbon-based nanomaterials (control, C), activated carbon (AC), 50 µg/mL CBN (50), or 100 µg/mL CBN (100). Callus cultures were grown in the presence of light or in the dark. CBNs tested were multiwalled carbon nanotubes (MWCNT) and graphene. Concentration is the average of three biological replicates presented as the average mg of vincristine per g dry weight (DW). $*p<0.05$, $**p<0.01$. Error bars represent standard error values.

Effect of CBN exposure on vincristine accumulation in *Catharanthus* callus: *Catharanthus*, in addition to making vinblastine, produces vincristine, an alkaloid used to treat cancers like acute leukemia, neuroblastoma, and Hodgkin lymphoma. We have used HPLC analysis to quantify the level of vincristine production in callus cultures of *Catharanthus roseus* exposed to CBNs. As seen in FIG. 11, graphene was the only CBN that significantly affected the accumulation of vincristine in *Catharanthus roseus* callus cultures. Inclusion of 50 μg/mL graphene in the medium increased *Catharanthus*' production of vincristine from an undetectable level in control samples to 1.5443 mg/g DW (p<0.05) when callus cultures were grown in the dark cultivation condition. Inclusion of 100 μg/mL graphene in medium of *Catharanthus roseus* callus grown in the dark cultivation condition increased vincristine from undetectable levels in control samples to 1.7150 mg/g DW (p<0.01). When *Catharanthus roseus* callus was grown in the light cultivation condition, exposure to 50 μg/mL graphene increased vincristine by 0.5630 mg/g DW (p<0.05) compared to control samples.

Vincristine and Vinblastine Accumulation in *Catharanthus* Callus in Relation to Initial Inoculum Weight To more accurately demonstrate the effect of CBN exposure on vinblastine and vincristine accumulation in callus cultures of *Catharanthus roseus*, we calculated the concentration of each alkaloid in relation to the initial weight of callus (200 mg). This calculation allowed us to determine the amount of either alkaloid produced by the initial inoculum of callus and more accurately depict the impact of CBN exposure on *Catharanthus roseus*.

Figure 12:
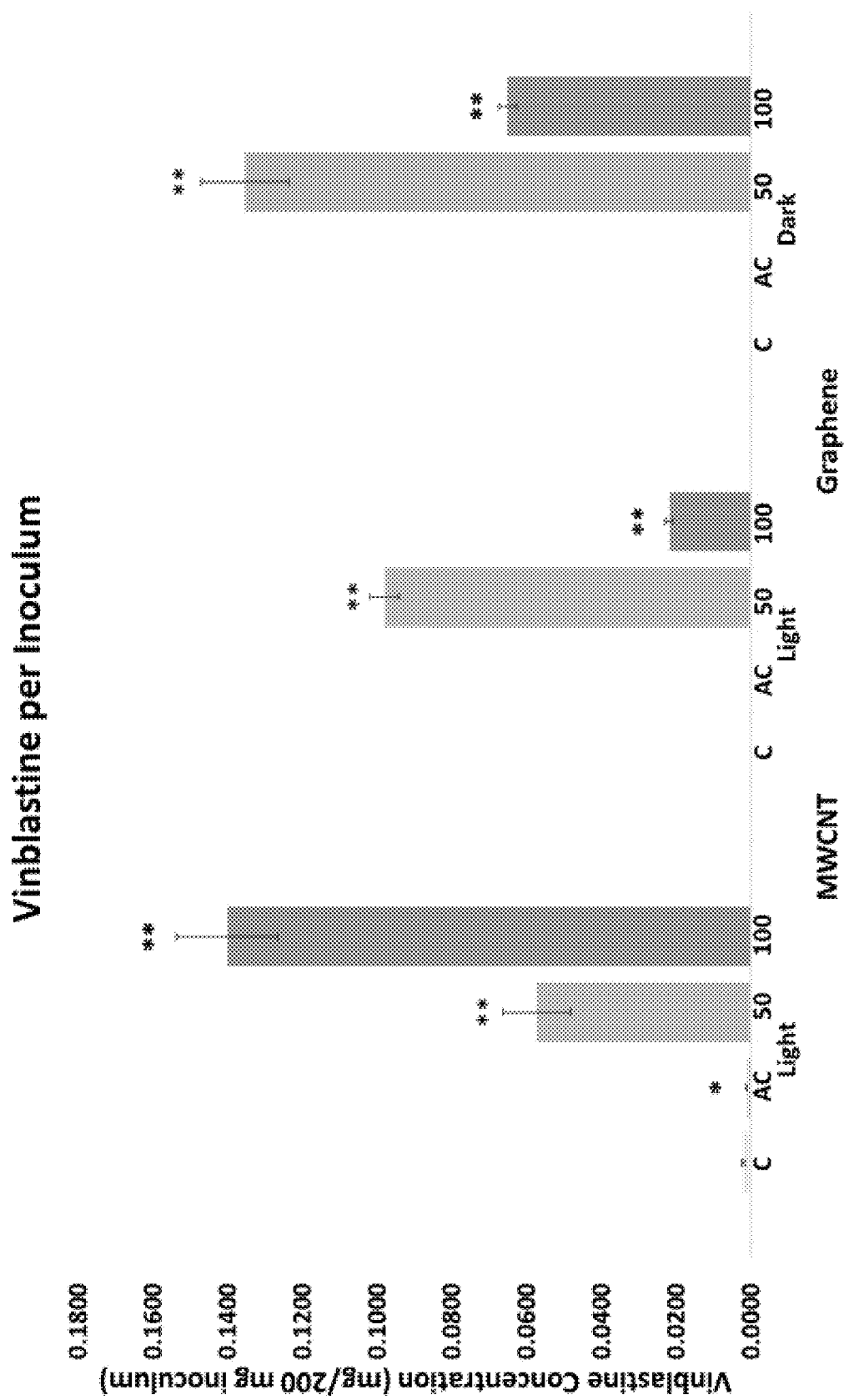
FIG. 12 shows the concentration of vinblastine in *Catharanthus roseus* callus cultures after 4 weeks of cultivation on media containing no carbon-based nanomaterials (control, C), activated carbon (AC), 50 µg/mL CBN (50), or 100 µg/mL CBN (100). Callus cultures were grown in the presence of light or in the dark. CBNs tested were multiwalled carbon nanotubes (MWCNT) and graphene. Concentration is the average of three biological replicates presented as the average mg of vinblastine per initial inoculum (200 mg). $*p<0.05$, $**p<0.01$. Error bars represent standard error values.

Vinblastine: As seen in FIG. 12, all CBNs dramatically increased the concentration of vinblastine in *Catharanthus roseus* callus cultures, independent of light or dark growth conditions. In control samples, vinblastine accumulated at very low or undetectable levels. Inclusion of 100 μg/mL MWCNT in medium resulted in the largest increase in vinblastine concentration when *Catharanthus roseus* callus was grown in the light cultivation condition. This exposure increased vinblastine from 0.0003 mg/200 mg inoculum to 0.1402 mg/200 mg inoculum (p<0.01).

Figure 13:
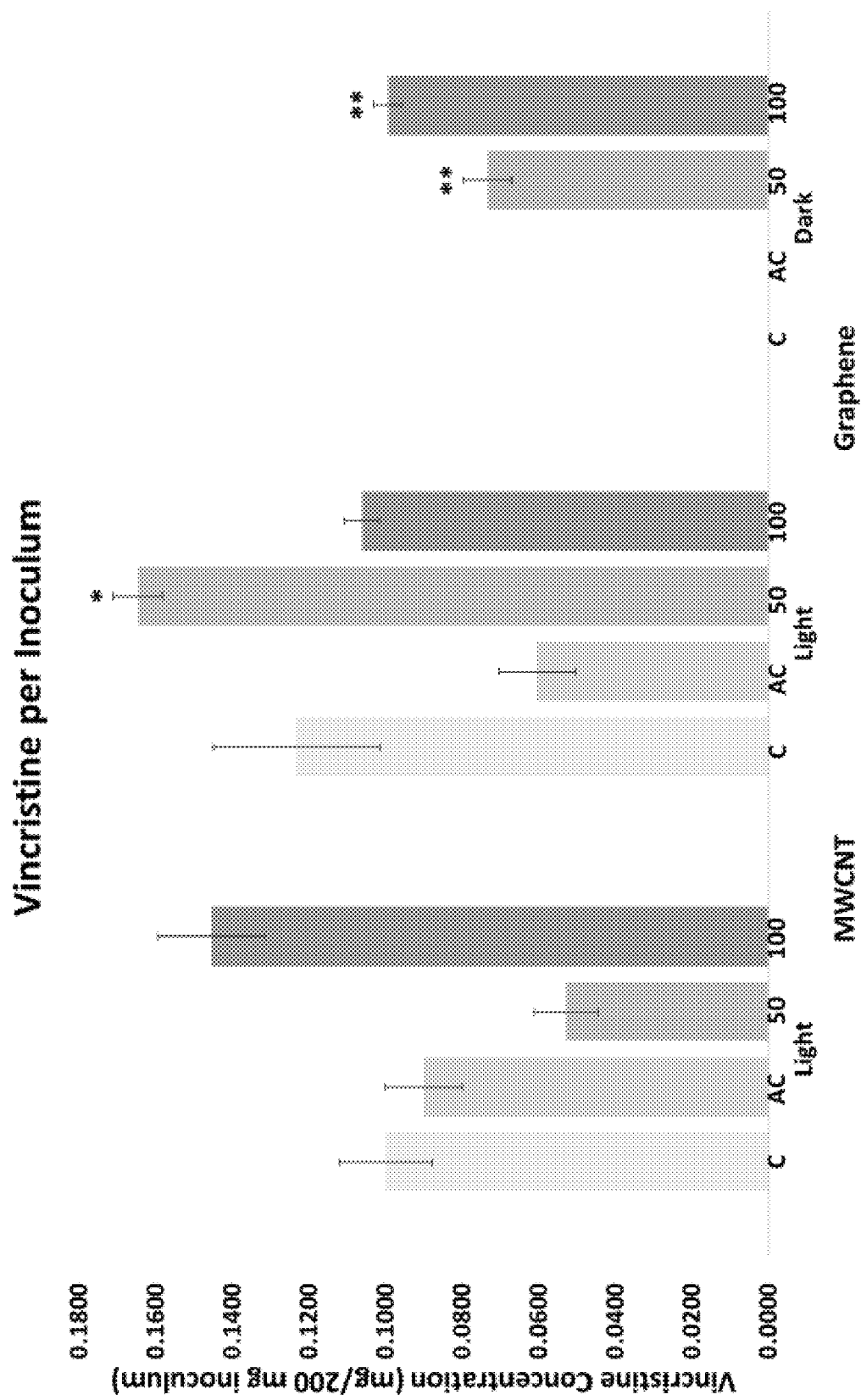
FIG. 13 shows the concentration of vincristine in *Catharanthus roseus* callus cultures after 4 weeks of cultivation on media containing no carbon-based nanomaterials (control, C), activated carbon (AC), 50 µg/mL CBN (50), or 100 µg/mL CBN (100). Callus cultures were grown in the presence of light or in the dark. CBNs tested were multiwalled carbon nanotubes (MWCNT) and graphene. Concentration is the average of three biological replicates presented as the average mg of vincristine per initial inoculum (200 mg). $*p<0.05$, $**p<0.01$. Error bars represent standard error values.

Vincristine: As seen in FIG. 13, graphene was the most effective material regarding an increase in vincristine concentration in *Catharanthus roseus* callus. Here, the largest increase of vincristine was seen with the addition of 50 μg/mL graphene when the *Catharanthus roseus* callus was grown in the light cultivation condition. This exposure increased vincristine from 0.1232 mg/200 mg inoculum in control samples to 0.1645 mg/200 mg inoculum in exposed samples (p<0.05).

The disclosure related to the significant effects that the MWCNTs have on plant gene expression raises important questions about the possible mechanisms that govern these effects. Previously, it was noted that many genes activated or inhibited by the MWCNTs in tomato plants are involved in plant stress-signal transduction and can be regulated by specific environmental stress [13]. Taking into account the ability of the MWCNTs to easily penetrate plant cell walls, it is hypothesized that plants can sense carbon nanotubes as stress factors similar to pathogen attacks, based on the experimental observations that carbon nanotubes can activate the same genes, as well as similar signaling pathways and cascades, which are normally activated in response to pathogen attacks [13]. However, new experimental data in the disclosure clearly show that the MWCNTs can also regulate the expression of genes that are involved in cell division/extension. These findings further highlight the fact that the effects that the MWCNTs have on plant gene expression are rather complex and require further investigation. These comprehensive studies focused on an understanding of how plant cells sense and recognize nano-sized materials at the molecular level. Therefore, a thorough comprehension of which signaling pathways are affected by nano-sized materials could result in a better understanding of the effects of the MWCNTs on plant transcriptome. Such findings could elucidate the impact that engineered nano-sized materials have on plant biology and could open a new research area at the interface between nano-sized materials, plant biology, disease control and treatment, and possibly the use of nanoscale agents for increase of drought tolerance.

These results according to embodiments of the disclosure therefore suggest that carbon nanotubes can regulate cell division and plant growth by a unique molecular mechanism that is related to the activation of water channels (aquaporins) and major gene regulators of cell division and extension. The inventors' previous findings have highlighted the positive effects of the MWCNTs on plant growth and development [12, 13]. The current data highlights novel positive effects of the MWCNTs at the cellular level and provides an understanding of the complex mechanism underlying the activation of plant growth. Applications may include enhanced production of plant cell cultures (suspensions, callus cultures) for the pharmaceutical industry, agro-biotechnology, or bioenergy industry. However, to consider the possible use of carbon nanoparticles in the food sector of agriculture, the consequences of the introduction of carbon nanotubes into the environment have to be thoroughly investigated. The detailed assessment of potential environmental risks of using carbon nano-sized materials in agriculture is a requirement in order to fully understand the positive or negative impact that such engineered nano-sized materials may have on agriculture. The data presented in this disclosure could further stimulate research focused on understanding the effects of carbon nanotubes on cell proliferation and on monitoring the expression of genes and proteins involved in cell division and water transport in other cell systems, such as those found in bacteria, animals, and fungi. The discovery of the mechanisms behind the effects that nano-sized materials have on the transcriptome and proteome of different types of cells is important for basic science and could be beneficial in the development of new biotechnologies.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the disclosure pertains without departing from its spirit and scope. Accordingly, the scope of the disclosure is defined by the appended claims rather than the foregoing description and the exemplary embodiments described therein.

REFERENCE LIST

[1]. Liu, H. K.; Wang, G. X.; Guo, Z.; Wang, J.; Konstantinov, K. Nano-sized materials for lithium-ion rechargeable batteries. J. Nanosci. Nanotechnol. 2006, 6, 1-15.

[2]. Wang, Y.; Mirkin, C. A.; Park, S. J. Nanofabrication beyond electronics. ACS Nano 2009, 26, 1049-1056.

[3]. Singh, S. Nanomedicine-nanoscale drugs and delivery systems. J. Nanosci. Nanotechnol. 2010, 10, 7906-7918.

[4]. Sozer, N.; Kokini, J. L. Nanotechnology and its applications in the food sector. Trends in Biotechnol. 2009, 27, 82-89.

[5]. Torney, F.; Trewyn, B.; Lin, V. S. Y.; Wang, K. Mesoporous silica nanoparticles deliver DNA and chemicals into plants. Nature Nanotechnol. 2007, 2, 295-300.

[6]. Gonzales-Melendi, P.; Fernandez-Pacheco, R.; Coronado, M. J.; Corredor, E.; Testillano, P. S.; Risueno, M. C.; Marquina, C.; Ibarra, M. P.; Rubiales, D.; Perez-De-Luque, A. Nanoparticles as smart treatment-delivery systems in plants: assessment of different techniques of microscopy for their visualization in plant tissues. Ann. Bot. 2008, 101, 187-195.

[7]. Liu, Q.; Chen, B.; Wang, Q.; Shi, X.; Xiao, Z.; Lin, J.; Fang, X. Carbon nanotubes as molecular transporters for walled plant cells. Nano Lett. 2009, 9, 1007-1010.

[8]. Serag, M. F.; Kaji, N.; Gaillard, C.; Okamoto, Y.; Terasaka, K.; Jabasini, M.; Tokeshi, M.; Mizukami, H.; Bianco, A.; Baba, Y. Trafficking and subcellular localization of multi-walled carbon nanotubes in plant cells. ACS Nano 2011, 5, 493-499.

[9]. Perez-de-Luque, A.; Rubiales, D. Nanotechnology for parasitic plant control. Pest Manag Sci. 2009, 65, 540-545.

[10]. Zheng, L.; Hong, F.; Lu, S.; Liu, C. Effect of nano-TiO2 on spinach of naturally aged seeds and growth of spinach. Biol. Trace Element Res. 2005, 104, 83-91.

[11]. Klaine, S. J.; Alvarez, P. J. J.; Batley, G. E.; Fernandes, T. F.; Handry, R. D.; Lyon, D. Y.; Manendra, S.; McKaughlin, M. J.; Lead, J. R. Nano-sized materials in the environment: behavior, fate bioavailability and effects. Environ. Toxicol. Chem. 2008, 27, 1825-1851.

[12]. Khodakovskaya, M.; Dervishi, E.; Mahmood, M.; Yang, X.; Li, Z.; Fumiya, W.; Biris, A. Carbon nanotubes are able to penetrate plant seed coat and dramatically affect seed germination and plant growth. ACS Nano 2009, 3, 3221-3227.

[13]. Khodakovskaya, M.; de Silva, K.; Nedosekin, D.; Dervishi, E.; Biris, A. S.; Shashkov, E. V.; Galanzha, E. I.; Zharov, V. P. Complex genetic, photothermal, and photoacoustic analysis of nanoparticle-plant interactions. PNAS 2011, 108, 1028-1033.

[14]. Das, A.; Chakraborty, B.; Sood, A. K. Raman spectroscopy of graphene on different substrates and influence of defects. Bull. Mater. Sci. 2008, 31(3), 579-584.

[15]. Reina, A.; Jia, X.; Ho, J.; Nezich, D.; Son, H.; Bulovic, V.; Dresselhaus M. S.; Kong, J. Large area, few-layer graphene films on arbitrary substrates by chemical vapor deposition. Nano Lett. 2009, 9(1), 30-35.

[16]. Biris, A. S.; Galanzha, E. I.; Li, Z.; Mahmood, M.; Zharov, V. P. In Vivo Raman Flow Cytometry for Real-

[17]. Khodakovskaya, M. V.; Bulgakov, V. P.; V. V. Makhan'kov, V. V. Effect of Phytohormones on Biomass Assumption and Contents of Ginsenosides in Callus Cultures Panax ginseng C. A. Mey. Biotechnology 1995, 9-10, 40-45.

[18]. Khodakovskaya, M. V.; Bulgakov, V. P.; Zhuravlev, Yu. N. The Effect of Some Metabolities of Isoprenoid Pathway on the Biomass Accumulation and Content of Ginsenosides in Ginseng Cell Cultures. Biotechnology 1997, 1, 42-47.

[19]. Thomas, T. D. The Role of Activated Charcoal in Plant Tissue Culture. Biotechnol. Adv. 2008, 26), 618-631.

[20]. Pan, M. J.; van Staden, J. The Use of Charcoal in in Vitro Culture-A Review. Plant Growth Regul. 1998, 26, 155-163.

[21]. Lin, C.; Fugetsu, B.; Su, Y.; Watari, F. Studies on Toxicity of Multi-walled Carbon Nanotubes on Arabidopsis T87 Suspension Cells. J. Hazardous Mater. 2009, 170, 578-583.

[22]. Tan, X-M,; Lin, C.; Fugetsu, B. Studies on Toxicity of Multi-walled Carbon Nanotubes on Suspension Rice Cells. Carbon 2009, 47, 3479-3487.

[23]. Alimohammadi, M.; Xu, Y.; Wang, D.; Biris, A. S.; Khodakovskaya, M. Physiological Responses Induced in Tomato Plants by a Two-Component Nanostructural System Composed of Carbon Nanotubes Conjugated with Quantum Dots and Its in Vivo Multimodal Detection. Nanotechnology 2011, 22), 295101.

[24]. Schnittger, A.; Schöbinger, U.; Stierhof, Y. D.; Hülskamp, M. Ectopic B-type Cyclin Expression Induces Mitotic Cycles in Endoreduplicating Arabidopsis Trichomes. Curr. Biol. 2002, 12, 415-420.

[25]. Tire, C.; de Rycke, R.; de Loose, M.; Inze, D.; Montagu, van; Englr, G. Extensin Gene Expression is Induced by Mechanical Stimuli Leading to Local Cell Wall Strengthening in Nicotiana plumbaginifolia. Planta 1994, 195, 175-181.

[26]. Merouropoulos, G.; Bennett, D. C.; Shitsat, A. H. The Arabidopsis Extensin Gene Is Developmentally Regulated, Is Induced by Wounding, Methyl Jasmonate, Abscisic and Salicylic Acid, and Codes for a Protein with Unusual Motifs. Planta 1999, 208, 212-219.

[27]. Salva, I.; Jamet, E. Expression of the Tobacco Ext 1.4 Extensin Gene upon Mechanical Constraint and Localization of Regulatory Regions. Plant Biol. 2001, 3, 32-41.

[28]. Bucher, M.; Brunner, S.; Zimmermann, P.; Zardi, G. I.; Amrhein, N.; Willmitzer, L.; Riesmeier, J. W. The Expression of an Extensin-like Protein Correlates with Cellular Tip Growth in Tomato. Plant Physiol. 2002, 128, 911-923.

[29]. Kaldenhoff, R.; Fischer, M. Aquaporins in Plants. Acta Physiol. 2006, 187, 169-176.

[30]. Maurel, C. Plant Aquaporins: Novel Functions and Regulation Properties. FEBS Lett. 2007, 581, 2227-2236.

[31]. Aharon, R.; Shahak, Y.; Wininger, S.; Bendov, R.; Kapulnik, Y.; Galili, G. Overexpression of a Plasma Membrane Aquaporin in Transgenic Tobacco Improves Plant Vigor under Favorable Growth Conditions but Not under Drought or Salt Stress. Plant Cell 2003, 15, 439-447.

[32]. Sade, N.; Vinocur, B. J.; Diber, A.; Shatil, A.; Ronen, G.; Nissan, H.; Wallach, R.; Karchi, H.; Moshelion, M. Improving Plant Stress Tolerance and Yield Production: Is the Tonoplast Aquaporin S1TIP2;2 a Key to Isohydric to Anisohydric Conversion. New Phytologist 2009, 181, 651-661.

[33]. Liu, H.-Y.; Yu, X.; Cui, D.-Y.; Sun, M.-H.; Sun, W.-N.; Tang, Z.-C.; Kwak, S.-S.; Su, W.-A. The Role of Water Channel Proteins and Nitric Oxide Signaling in Rice Seed Germination. Cell Res. 2007, 17, 638-649.

[34]. Kumar, S.; Bajpai, V.; Singh, A.; Kumar, B. Identification, Characterization and Distribution of Terpene Indole Alkaloids in Ethanolic Extracts of Catharanthus Roseus Using HPLC/ESI-QTOF-MS/MS and the Study of Their Geographical Variation. Rapid Commun. Mass Spectrom. 2017 DOI: 10.1002/rcm.8037.

[35]. Dervishi, E.; Li, Z.; Biris, A. R.; Lupu, D.; Trigwell, S.; Biris, A. S. Morphology of Multi-walled Carbon Nanotubes Affected by the Thermal Stability of the Catalyst System. Chem. Mater. 2007, 19, 179-184.

[36]. Biris, A. S.; Schmitt, T. C.; Little, R. B.; Li, Z.; Xu, Y.; Biris, A. R.; Lupu, D.; Dervishi, E.; Trigwell, S.; Miller, D. W.; Rahman, Z. Influence of the RF Excitation of the Catalyst System on the Morphology of Multi-walled Carbon Nanotubes. J. Phys. Chem. C 2007, 111), 17970-17975.

[37]. Li, Z.; Dervishi, E.; Xu, Y.; Ma, X.; Saini, V.; Biris, A. S.; Little, R.; Biris, A. R.; Lupu, D. Effects of the Fe—Co Interaction on the Growth of Multiwall Carbon Nanotubes. J. Chem. Phys. 2008, 129, 074712.

[38]. Biris, A. R.; Biris, A. S.; Lupu, D.; Trigwell, S.; Dervishi, E.; Rahman, Z.; Marginean, P. Catalyst Excitation by Radio Frequency for Improved Carbon Nanotubes Synthesis. Chem. Phys. Lett. 2006, 429, 204-208.

[39]. Khodakovskaya, M.; Sword, C.; Perera, I.; Boss, W.; Brown, C.; Sederoff, H. Expression of Inositol-1,4,5-Triphosphate Metabolism Affects Drought Tolerance, Carbohydrate Metabolism, and Phosphate-Sensitive Biomass Increases in Tomato. Plant Biotechnol. J. 2010, 8, 170-183.

[40]. de Silva, K.; Laska, B.; Brown, C.; Winter Sederoff, H.; Khodakovskaya, M. Arabidopsis thaliana Calcium-Dependent Lipid-Binding Protein (AtCLB); A Novel Repressor of Abiotic Stress Response. J. Exp. Bot. 2011, 62, 2679-2689.

[41]. Monforte González, M.; Ayora Talavera, T.; Maldonado Mendoza, I. E.; Loyola Vargas, V. M. Quantitative Analysis of Serpentine and Ajmalicine in Plant Tissues of Catharanthus Roseus and Hyoscyamine and Scopolamine in Root Tissues of Datura Stramonium by Thin Layer Chromatography densitometry. Phytochem. Anal. 1992, 3 (3), 117-121 DOI: 10.1002/pca.2800030305.

| SEQUENCE LIST |
| --- |
| No. 1 |
| 5'-AGCCACCACCATACACACCTCAAT-3' |
| No. 2 |
| 5'-TGGTGGTGAAGACGGTGTCACATA-3' |
| No. 3 |
| 5'-GGTTCATTTGGCCACCATCCCAAT-3' |
| No. 4 |
| 5'-GCAGCAAGAGCAGCTCCAATGAAT-3' |
| No. 5 |
| 5'-TTCTGGCTGAGCTGGGATTGATGA-3' |

SEQUENCE LIST

No. 6
5'-TGATGGTGTGTCGAGCAGCATAGA-3'

No. 7
5'-GAACGGGAAATTGTCCGCGATGTT-3'

SEQUENCE LIST

No. 8
5'-ATGGTAATGACCTGCCCATCTGGT-3'.

What is claimed is:

1. A method for production of alkaloid in Catharanthus cell culture, comprising:
    providing a cell culture having one or more cells of a Catharanthus plant;
    introducing an amount of a nano-sized material into the cell culture to form a mixture thereof;
    maintaining the mixture at a temperature for a period of time to allow sufficient interaction of the one or more cells with the nano-sized material so as to enhance the production of the alkaloid in the cell culture; and
    extracting the alkaloid from the cell culture,
    wherein the nano-sized material comprises at least multi-walled carbon nanotubes having a purity of about 98% and a diameter of about 20 nm; and
    wherein the nano-sized material has a concentration in a range of 5-100 g/mL in the cell culture.

2. The method of claim 1, wherein the step of providing the cell culture further comprising:
    germinating seeds of the plant in a Murashige-Skoog (MS) medium to establish calli of the plant; and
    maintaining the callus culture at a predetermined condition to produce the cell culture having the one or more cells of the plant.

3. The method of claim 1, wherein the alkaloid includes vinblastine and/or vincristine.

4. The method of claim 1, further comprising maintaining the nano-sized material and the cell culture mixture in the light cultivation condition.

5. The method of claim 1, wherein the temperature is in a range of 5–35° C., and the period of time is in a range from 0.1 hours to 2 months.

6. The method of claim 1, wherein the amount of the nano-sized material has a concentration in a range of 25-100 μg/mL in the cell culture.

7. A method for enhancing production of an alkaloid in a Catharanthus cell culture, comprising:
    providing a cell culture having one or more cells of a Catharanthus plant;
    introducing an amount of a nano-sized material into the cell culture to form a mixture thereof; and
    maintaining the mixture at a temperature for a period of time to allow sufficient interaction of the one or more cells with the nano-sized material so as to enhance the production of the alkaloid in the cell culture,
    wherein the nano-sized material comprises multi-walled carbon nanotubes having a purity of about 98% and a diameter of about 20 nm; and
    wherein the nano-sized material has a concentration in a range of 5-100 g/mL in the cell culture.

8. The method of claim 7, wherein the amount of the nano-sized material has a concentration in a range of 25-100 μg/mL in the cell culture.

9. The method of claim 7, further comprising maintaining the nano-sized material and the cell culture mixture in the light cultivation condition.

10. The method of claim 7, wherein the temperature is in a range of 5–35° C., and the period of time is in a range from 0.1 hours to 2 months.

\* \* \* \* \*